US011756657B2

(12) United States Patent
Irish et al.

(10) Patent No.: US 11,756,657 B2
(45) Date of Patent: Sep. 12, 2023

(54) SYSTEM AND METHOD FOR DISPLAY OF LABORATORY DATA

(71) Applicant: Draeger Medical Systems, Inc., Andover, MA (US)

(72) Inventors: Mark Irish, Moorestown, NJ (US); Carl William Sisco, Milan, TN (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 126 days.

(21) Appl. No.: 16/598,521

(22) Filed: Oct. 10, 2019

(65) Prior Publication Data

US 2020/0118652 A1      Apr. 16, 2020

Related U.S. Application Data

(60) Provisional application No. 62/743,819, filed on Oct. 10, 2018.

(51) Int. Cl.
| | |
|---|---|
| *G16H 10/40* | (2018.01) |
| *G16H 10/60* | (2018.01) |
| *G06F 3/0481* | (2022.01) |
| *G06F 3/0484* | (2022.01) |
| *G16H 30/20* | (2018.01) |

(52) U.S. Cl.
CPC ........... *G16H 10/40* (2018.01); *G06F 3/0481* (2013.01); *G06F 3/0484* (2013.01); *G16H 10/60* (2018.01); *G16H 30/20* (2018.01)

(58) Field of Classification Search
CPC ........ G16H 10/40; G16H 10/60; G16H 30/20; G06F 3/0481; G06F 3/0484

USPC .......................................................... 705/2, 3
See application file for complete search history.

(56) References Cited

U.S. PATENT DOCUMENTS

| | | | |
|---|---|---|---|
| 2002/0186238 A1 | 12/2002 | Sylor et al. | |
| 2009/0054735 A1* | 2/2009 | Higgins | A61B 5/0006 600/300 |
| 2010/0131883 A1* | 5/2010 | Linthicum | G16H 40/63 715/771 |

(Continued)

OTHER PUBLICATIONS

Imhoff M, Kuhls S. Alarm algorithms in critical care monitoring. Anesth Analg. May 2006;102(5):1525-37. doi: 10.1213/01.ane. 0000204385.01983.61. PMID: 16632837. (Year: 2006).*

(Continued)

*Primary Examiner* — Joshua B Blanchette
(74) *Attorney, Agent, or Firm* — Nolte Lackenbach Siegel

(57) ABSTRACT

A system for use with a user interface system, a first data provider, a second data provider and a display device. The system comprises a data input component, a fishbone diagram generating component, an output component, a user interface component, and a data trend generating component. The data trend generating component can generate data trend image data based on a trends diagram instruction. The output component can further output the data trend image data to the display device to be displayed so as to include a first graphical function and a second graphical function, wherein the first graphical function corresponds to first patient laboratory test data, and wherein the second graphical function corresponds to second patient laboratory test data.

27 Claims, 15 Drawing Sheets

(56) References Cited

U.S. PATENT DOCUMENTS

2015/0257716 A1* 9/2015 Humphrys ............ G16H 40/63
600/301

OTHER PUBLICATIONS

"Critical Care Transport User Group Meeting", AMTC 2012, retrieved from https://www.emscharts.com/pub/event-CCTUserGroup-2012.cfm, published Aug. 19, 2014.
"RCA of Incident: ENT to Histo/Cyto 15-day Sample Delay to Sarawak General Hospital", retrieved from https://www.slideshare.net/alexanderbeemermijen/rca-oct-2012-hpe, published Oct. 3, 2013.
"Visualizing Lab Results", retrieved from http://qlikdork.com/2015/01/visualizing-lab-results, published Jan. 8, 2015.

* cited by examiner

FIG. 5

SYSTEM AND METHOD FOR DISPLAY OF LABORATORY DATA

CROSS REFERENCE TO RELATED APPLICATIONS

Priority is claimed to U.S. Provisional Application 62/743,819, filed Oct. 10, 2018.

TECHNICAL FIELD

Embodiments of this disclosure relate to systems and methods for charting and managing anesthesia cases in the operating room or anywhere anesthesia is administered.

BACKGROUND

Today's increasingly integrated healthcare environment places more demands on the anesthesia provider. In addition, the interaction between the anesthesia workplace and the rest of the hospital is increasingly complex. Fortunately, there are tools to automatically capture patient's vital signs or patient parameters in all phases of the operative process (e.g., preoperative, operative and perioperative care) as well as incorporate vital signs data into, for example, the patient's electronic medical record (EMR). Advantageously, automated capture of patient parameter data reduces staff workload and frees the anesthesia provider's time for increased patient vigilance and direct patient care.

In this environment, the anesthesia providers need to make rapid decisions on how to treat a patient, particularly in long and complex operational cases. There is a need to efficiently present and organize real-time, patient parameter data to the anesthesia provider in order to assess the impact on the patient due to the anesthesia providers' treatment decisions.

SUMMARY

To fulfill the need as described above of organizing and presenting clinical laboratory data to the anesthesia providers and other technical needs, the present disclosure provides a system and method for delivering clinical laboratory data to anesthesia providers continually throughout all phases of operative process (e.g., preoperative, operative and perioperative care) and acute care. By presenting data sorted into clinical specialties (e.g., hematology, chemistry, etc.), using fishbone or analogous visual diagrams and providing trend charts, the anesthesia provider can more rapidly assess and interpret incoming data. Aspects of the present disclosure are particularly useful in extremely critical surgeries (e.g., heart and liver transplants, etc.) requiring precise monitoring and management of patient's condition.

An aspect of the present disclosure is drawn to a system for use with a user interface system. The system may include one or more of the following features. The system may include a first data provider, a second data provider and a display device, wherein the user interface system being operable to provide user interface instructions, wherein the first data provider providing first patient laboratory test data, wherein the second data provider providing second patient laboratory test data, wherein the display device is operable to display first image data, to display second image data and to display third image data, wherein the first patient laboratory test data corresponds to a first measurable parameter associated with a patient and includes a first plurality of test data values over a time period, wherein the second patient laboratory test data corresponds to a second measurable parameter associated with the patient and includes a second plurality of test data values over the time period. The system may comprise a data input component, a fishbone or analogous visual diagram generating component, an output component, a user interface component, and a data trend generating component. The data input component can receive the first patient laboratory test data and the second patient laboratory test data. The fishbone or analogous visual diagram generating component can generate corresponding diagram image data associated with the first patient laboratory test data and the second patient laboratory test data. The output component can output the fishbone or analogous visual diagram image data to the display device to be displayed as the first image data so as to include a first fishbone diagram section and a second fishbone diagram section, wherein the first fishbone diagram section corresponds to the first patient laboratory test data, and wherein the second fishbone diagram section corresponds to the second patient laboratory test data. The user interface component can generate a trends diagram instruction based on the user interface instructions. The data trend generating component can generate data trend image data based on the trends diagram instruction, wherein the data trend image data is based on the first patient laboratory test data and the second patient laboratory test data. The output component can further output the data trend image data to the display device to be displayed as the second image data so as to include a first graphical function and a second graphical function, wherein the first graphical function corresponds to the first patient laboratory test data, and wherein the second graphical function corresponds to the second patient laboratory test data. The user interface component can further enable selection of the first image data. The output component can further output the data trend image data to the display device to be displayed as the second image data based on the selection of the first image data.

BRIEF DESCRIPTION OF THE DRAWINGS

The accompanying drawings, which are incorporated in and form a part of the specification, illustrate example embodiments and, together with the description, serve to explain the principles of this disclosure. In the drawings:

FIGS. 2A-2D illustrate a system for anesthesia information management in accordance with aspects of the present disclosure, wherein FIG. 2A illustrates the system at a time $t_1$, FIG. 2B illustrates the system at a time $t_2$, FIG. 2C illustrates the system at a time $t_3$ and FIG. 2D illustrates the system at a time $t_4$;

FIG. 5 illustrates an example image display in accordance with an aspect of the present disclosure;

FIGS. 6A-B illustrate example data trend images in accordance with aspects of the present disclosure, wherein FIG. 6A illustrates an example data trend image and FIG. 6B illustrates another example data trend image; and FIGS. 7A-E illustrate an example method of overlaying data trend images in accordance with aspects of the present disclosure, wherein FIG. 7A illustrates an example data trend image and another example data trend image at a time $t_a$, FIG. 7B illustrates the example data trend image and the other example data trend image at a time $t_b$, FIG. 7C illustrates the example data trend image and the other example data trend image at a time $t_c$, FIG. 7D illustrates the example data trend image and the other example data trend image at a time $t_d$ and FIG. 7E illustrates the example data trend image and the other example data trend image at a time $t_e$.

DETAILED DESCRIPTION

Figure 1:
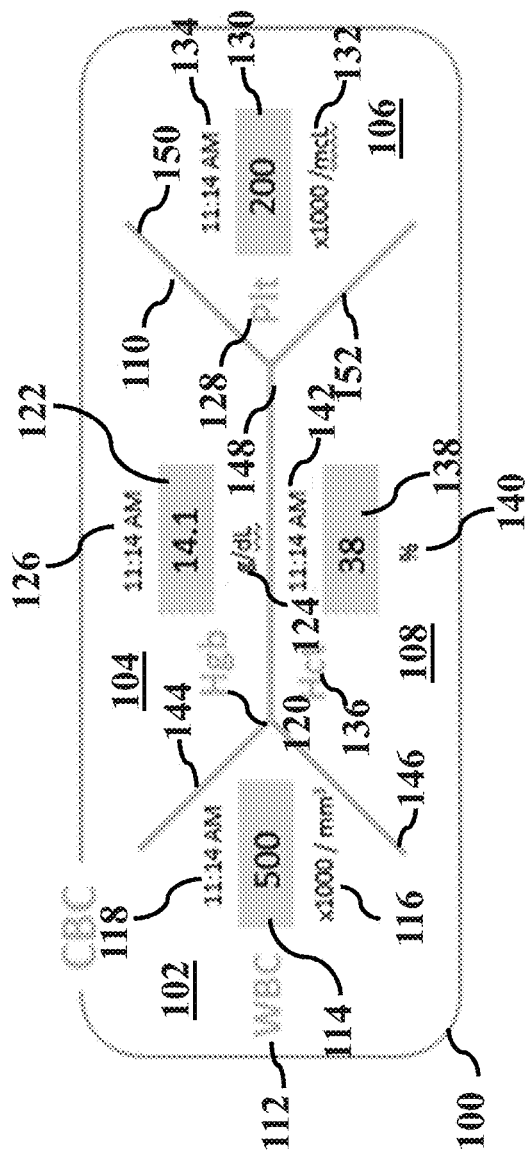
FIG. 1 illustrates a complete blood count (CBC) lab panel.

During a surgical case an anesthesia information management system (AIMS) electronically receives laboratory results for the patient, for example from a facility's Electronic Medical Records (EMR) system. Additionally, any laboratory results or other parameters of a patient that are generated from monitoring and/or therapeutic devices within the anesthesia care location may be input automatically or manually into the patient record.

Figure 5:
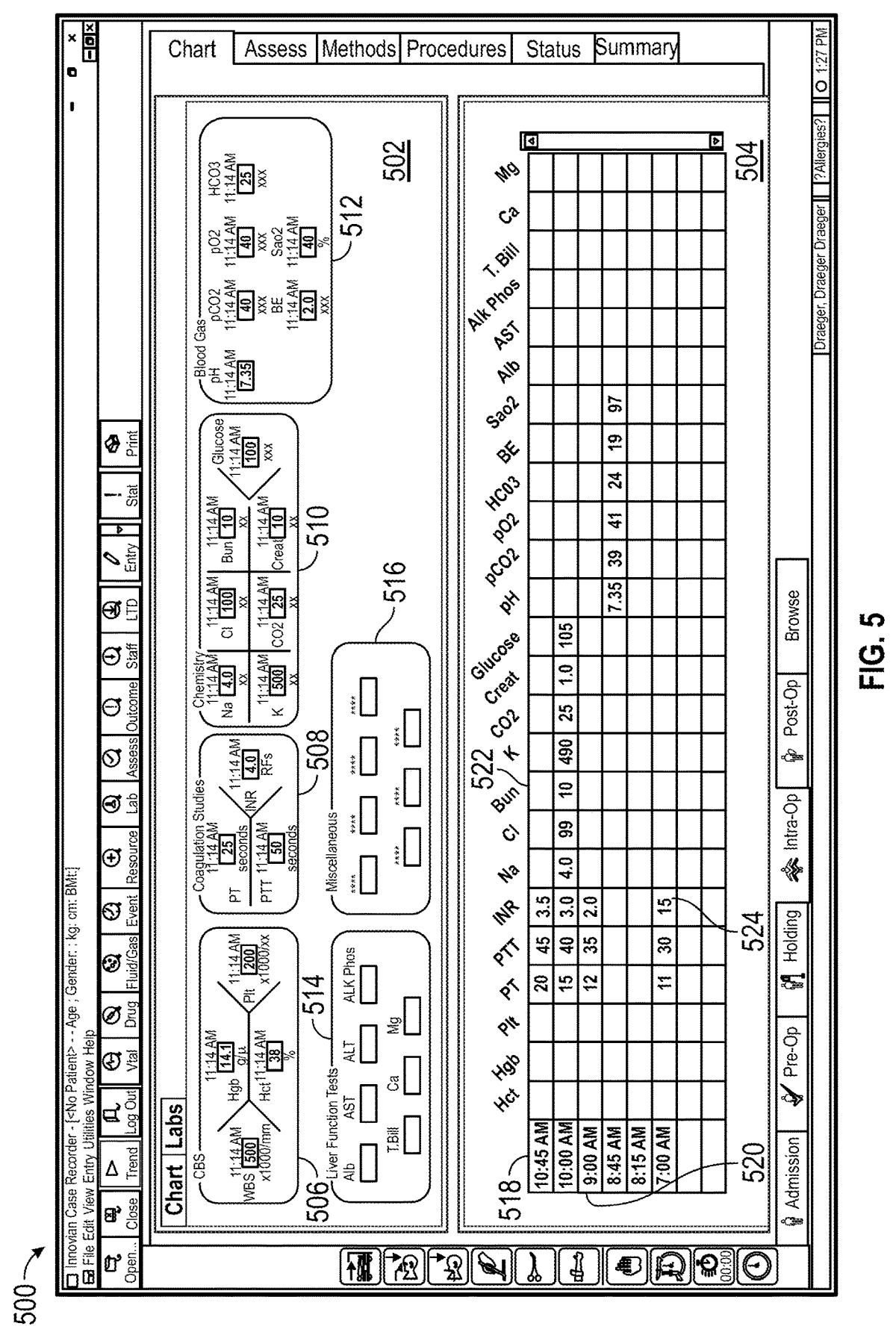

Within AIMS, an image display is dedicated to providing laboratory test results, with reference to FIG. 5 which will be further described in detail.

One section of the image display may present the data in fishbone or analogous visual diagrams for each specialty including, but not limited to: hematologic parameters including, but not limited to, red blood cell count, hemoglobin concentration, white blood cell count, differential white blood cell count, platelet count, hematocrit, mean corpuscular volume, mean corpuscular hemoglobin, mean corpuscular hemoglobin concentration and differential leukocyte count; coagulation parameters including, but not limited to, prothrombin time (PT), partial thromboplastin time (PTT), internal normalized ratio (INR), fibrinogen, anti-thrombin time, overall activity of vitamin-K-dependency and other coagulation factors; clinical chemistry parameters including but not limited to electrolytes, i.e. potassium (K), sodium (Na), calcium (Ca), chloride (Cl) and phosphorus (P). Further, the clinical chemistry parameters may include glucose, lactate, total cholesterol, blood urea nitrogen (Bun), creatinine (Creat), total protein, total bilirubin (T. Bili), carbon dioxide ($CO_2$), albumin (Alb), hepatic enzymes (e.g., alanine aminotransferase (ALT), aspartate aminotransferase (AST), alkaline phosphatase (Alk Phos), sorbitol dehydrogenase, and gamma-glutamyl transferase), reticulocyte count and bone marrow cytology; blood gas parameters including but not limited to hydrogen ion concentrations in blood (pH), partial pressure of oxygen ($pO_2$), partial pressure of carbon dioxide ($pCO_2$), bicarbonate level ($HCO_3$—), base excess (BE) and fraction of inspired oxygen ($FiO_2$); liver function-associated parameters including, but not limited to, heparin, Alb, AST, ALT, Alk Phos, T. Bili, calcium (Ca) and magnesium (Mg); and other miscellaneous laboratory tests related to the blood of the patient such as pregnancy test results.

Each section of the fishbone or analogous visual diagram may include a specific laboratory test within that grouping. The diagram may include at least one parameter in a grouping of laboratory tests, as described above. For example, the diagram may include at least one of WBC, Hgb, Hct and Plt in the grouping of hematologic parameters. In another exemplary embodiment, the diagram may include at least one of PT, PTT and INR in the grouping of coagulation parameters. In another exemplary embodiment, the diagram may include at least one of Na, Cl, Bun, K, $CO_2$, Creat and Glucose in the grouping of clinical chemistry parameters. In another exemplary embodiment, the diagram may include at least one of pH, $pCO_2$, $pO_2$, $HCO_3$, BE and Sao2 in the grouping of blood gas parameters. In another embodiment, the diagram may include at least one of Alb, AST, ALT, Alk Phos, T. Bili, Ca and Mg in the grouping of liver function test parameters. In another embodiment, the diagram may include at least the results of a pregnancy test in the groups of miscellaneous laboratory tests. In the diagram, each test result may be displayed along with the time the result was measured or received and the corresponding unit of measure.

Alternatively, the diagram is not limited to display of parameters within a single grouping, that is, the diagram may include parameters from different groupings of laboratory tests. For example, the diagram may include at least one parameter from various groups of laboratory tests including hematologic parameters, coagulation parameters, clinical chemistry parameters, blood gas parameters and pregnancy tests.

In the anesthesia workplace, much more information about a patient's laboratory reports and other associated parameters may be needed for the anesthesia provider to assess the patient's condition and determine proper treatment, thereby improving care for the patient. Accordingly, one aspect of the present disclosure further provides a data management system and method for electronically collecting and displaying preoperative, operative and perioperative care information. The anesthesia providers, including anesthesiologists, Certified Registered Nurse Anesthetists (CRNAs), Registered Nurses (RNs) and other qualified clinical personnel, may use a data management system and method in accordance with aspects of the present disclosure to document an acute care preoperative anesthesia process, an acute care operative anesthesia process and acute care perioperative anesthesia process.

When a patient is going to undergo a surgical procedure wherein anesthesia will be provided, it is critical that the anesthesia provider understand the patient's far and near term medical history and physiological status. An AIMS system and method in accordance with aspects of the present disclosure enables the creation, access and modification of a patient's medical history and physiological status in order to provide optimal preoperative, operative and perioperative care.

The present disclosure further provides a historical table of all laboratory test results that have been received by the AIMS during the surgical case in another section of the image display. In one embodiment, the historical table is organized such that the y-axis displays the time when a result was received, the x-axis provides the list of available laboratory test results. Laboratory tests along the x-axis are organized in the same groupings that are displayed in the fishbone diagrams. For example, all hematology related tests are presented next to each other. If the list on the x or y axis exceeds the area available for display, scroll bars will appear allowing the user to scroll and view the desired data. It should be understood the organization of the historical table described herein is for exemplary purposes only, and not intended to limit the scope of the present disclosure. The historical table may be configurable by the user, and may allow manual entry by one or more users of laboratory test results and therapies of the patient associated with a date and time.

The use of the fishbone or similar types of visual diagrams provides the anesthesia provider real-time feedback on such treatment decisions as well as provides flexibility in viewing patient parameter information either numerically, graphically, or combinations thereof. In one aspect, a fishbone or analogous visual diagram may highlight one or more critical parameters in a patient's laboratory test. The parameters may be within a specific grouping of laboratory tests. Alternatively, it may include important and/or representative parameters in different groupings of laboratory tests. Upon the selection of the visual diagram by the anesthesia provider, it further enables the display of data trend of each patient parameter shown in the diagram over a certain period of time. The visual diagram and/or the corresponding trend graphs may allow the anesthesia provider to have rapid visual assessments of any critical changes during preoperative, operative and perioperative care. For example, the visual diagram and/or trend graphs may provide reference points of the parameter being displayed as well as any change that has been taken place, such that the anesthesia provider may be able to correlate with the patient's conditions during all phases of the operational process.

It may be substantially advantageous in long and complex operational cases such as liver transplants, heart surgery and Trauma and Cardio-Pulmonary Bypass (CPB), where changes in certain parameters over time are critical. In such instances, a trend graph would permit rapid visual assessments of any critical changes in the patient's parameters to precisely monitor and manage the patient's condition. For example, during a liver transplants operation or CPB process, the disclosed system and method of organizing and displaying visual diagrams including laboratory test results (e.g., heparin concentration) may allow the anesthesia provider continuously receive and monitor the results at a substantially constant rate. The laboratory results displayed in the visual diagram and/or trend graphs may allow the anesthesia provider to determine e.g., how much heparin to be given to the patient during the bypass, whether another unit of blood may be needed or not, the amount of the blood given to the patient is so large that there may not be enough coagulation factors available to form a clot (platelets, fibrinogen, etc.).

Furthermore, the described system and method of organizing and displaying visual diagrams and corresponding trend graphs for laboratory tests may provide additional functions for organizing and configuring laboratory test results, such that the test results corresponding to a plurality of parameters each measured or received at different time are configured and displayed upon the facilities acceptable range of values. For example, each time a new set of laboratory test results are generated, the older values are automatically moved to at least one of the trend graph, the historical table or a spreadsheet. Therefore, the provider may easily view a most recently generated laboratory results displayed in the visual diagram, and the trending of the corresponding parameter over time.

FIG. 1 illustrates a complete blood count (CBC) lab panel 100 arranged in a fishbone diagram. As described in detail below, the fishbone diagram may allow a caregiver (e.g., an anesthesia provider) to have rapid visual assessments of any critical changes during preoperative, operative and perioperative care. For example, the fishbone diagram may allow the anesthesia provider to easily view parameters necessary for continuous monitoring of a patient undergoing general anesthesia.

As shown in the figure, lab panel 100 includes a measurable parameter section 102, a measurable parameter section 104, a measurable parameter section 106, a measurable parameter section 108, and a fishbone skeleton 110.

Measurable parameter section 102 includes a measurable parameter identifier 112, a measurable parameter value 114, a measurable parameter unit 116 and a timestamp 118. A measurable parameter identifier identifies the parameter of the patient that has been measured. A measurable parameter value is the most recently received value of the parameter of the patient that has been measured. A measurable parameter unit is the dimensional unit of the measurable parameter value. A timestamp is the time at which the most recently received measurable parameter value was obtained, measured, or provided. It should be noted that in some cases, a timestamp may include a day or date.

In this example embodiment: measurable parameter identifier 112 is "WBC," which is an acronym for white blood cell count; measurable parameter value 114 is 500; measurable parameter unit 116 is $\times 1000/mm^3$; and timestamp 118 is 11:14 AM.

Measurable parameter section 104 includes a measurable parameter identifier 120, a measurable parameter value 122, a measurable parameter unit 124 and a timestamp 126. In this example embodiment: measurable parameter identifier 120 is "Hgb," which is an abbreviation for hemoglobin; measurable parameter value 122 is 14.1; measurable parameter unit 124 is g/dl; and timestamp 126 is 11:14 AM.

Measurable parameter section 106 includes a measurable parameter identifier 128, a measurable parameter value 130, a measurable parameter unit 132 and a timestamp 134. In this example embodiment: measurable parameter identifier 128 is "Plt," which is an abbreviation for platelets; measurable parameter value 130 is 200; measurable parameter unit 132 is $\times 1000/mcL$; and timestamp 134 is 11:14 AM.

Measurable parameter section 108 includes a measurable parameter identifier 136, a measurable parameter value 138, a measurable parameter unit 140 and a timestamp 142. In this example embodiment: measurable parameter identifier 136 is "Hct," which is an abbreviation for hematocrit; measurable parameter value 138 is 38; measurable parameter unit 140 is %; and timestamp 142 is 11:14 AM.

Fishbone skeleton 110 includes a segment 144, a segment 146, a segment 148, a segment 150 and a segment 152. Segments 144 and 146 are arranged to connect so as to form a "V" shape providing a demarcated area for measurable parameter section 102. Segments 150 and 152 are arranged to connect so as to form a "V" shape providing a demarcated area for measurable parameter section 106. One end of segment 148 is connected to segments 144 and 146, whereas the other end of segment 148 is connected to segments 150 and 152 so as to provide a demarcated area for measurable parameter section 104 and so as to provide a demarcated area for measurable parameter section 108.

Lab panels, such as lab panel 100 above, are used in reporting lab results. This placement of laboratory results in the diagram is consistent between labs and hospitals resulting in quick and easy to read lab reports.

It should be understood the present disclosure is not limited to the fishbone diagrams described herein. The above-described benefits of the present disclosure may be realized by a non-fishbone diagram such a star diagram or rectangular diagram in which parameters are displayed in a manner that the anesthesia provider has quick and clear understandings. One of ordinary skill in the art would understand that various types of non-fishbone diagrams are within the scope of the present disclosure.

Aspects of the present disclosure will now be described with reference to FIGS. 2A-7E.

Figure 2A:
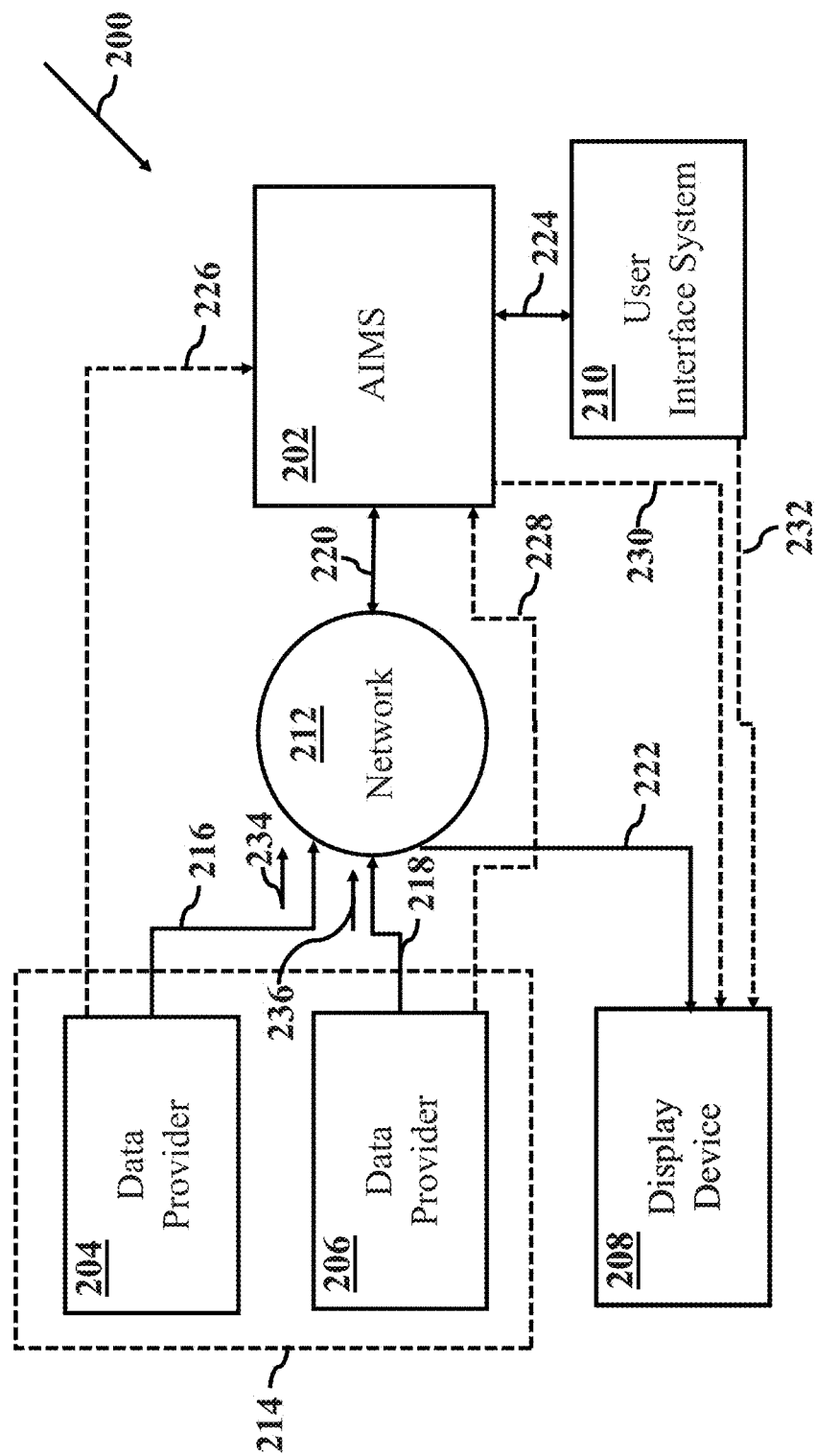
Figure 2B:
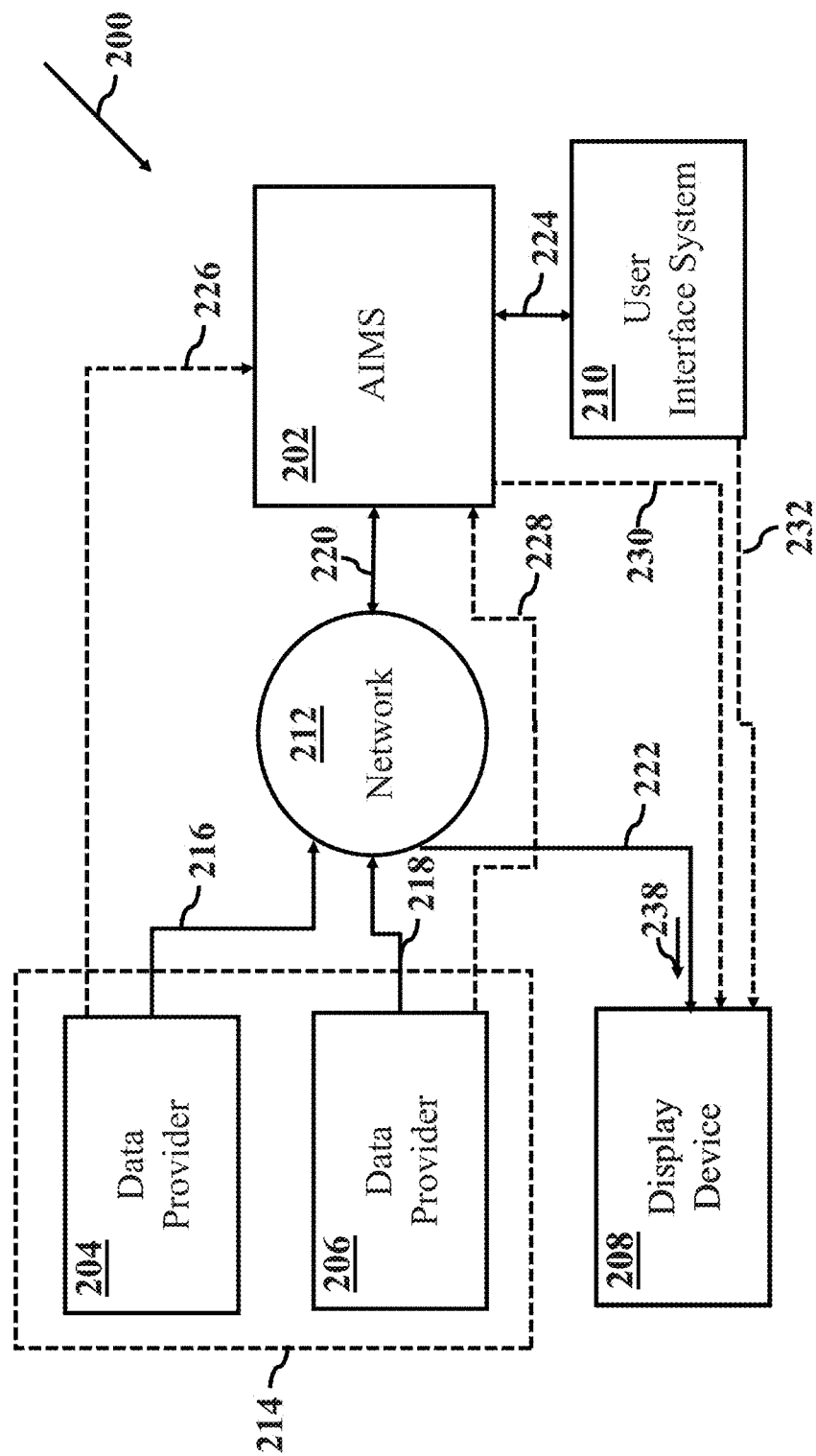
Figure 2C:
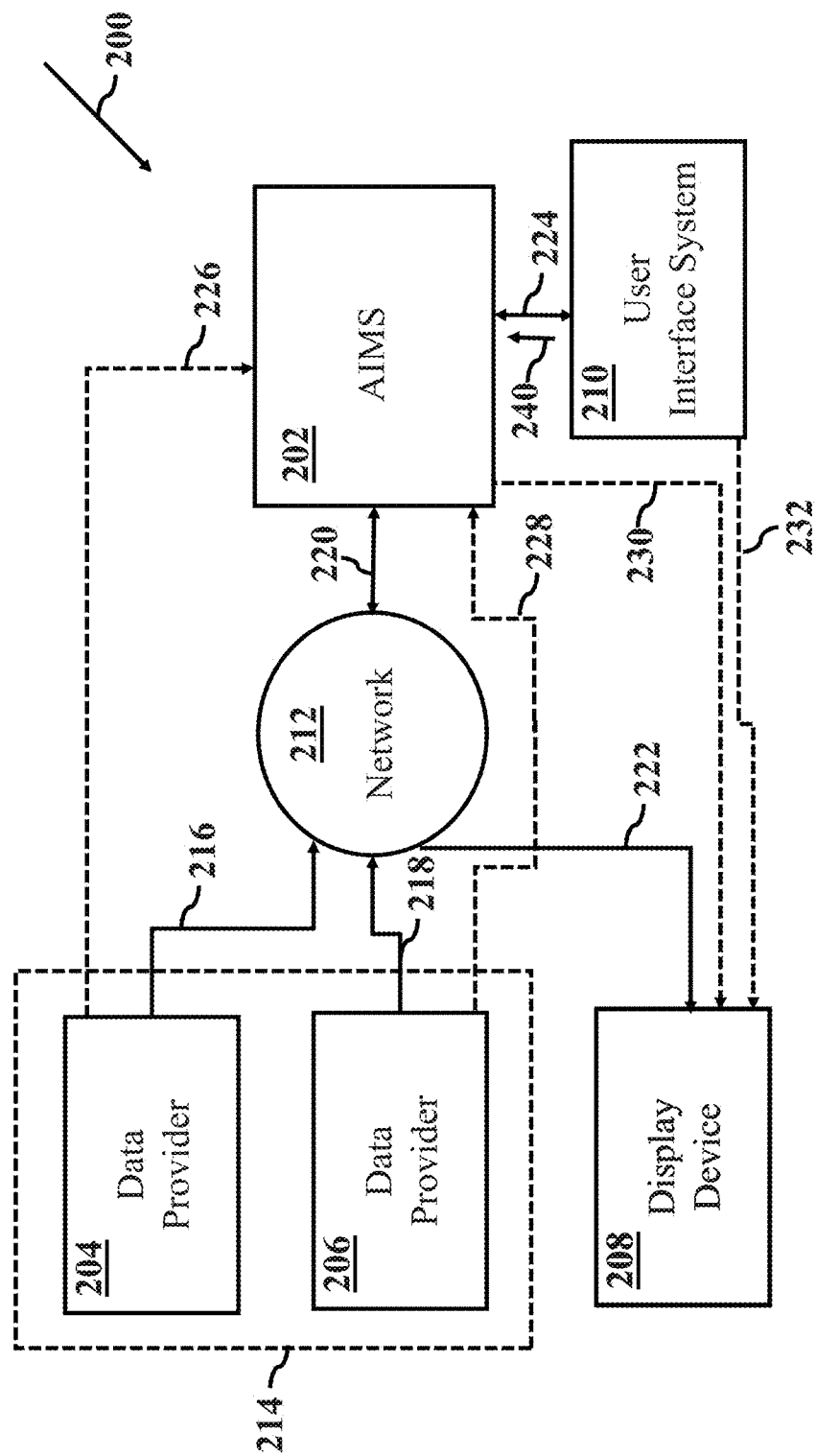
Figure 2D:
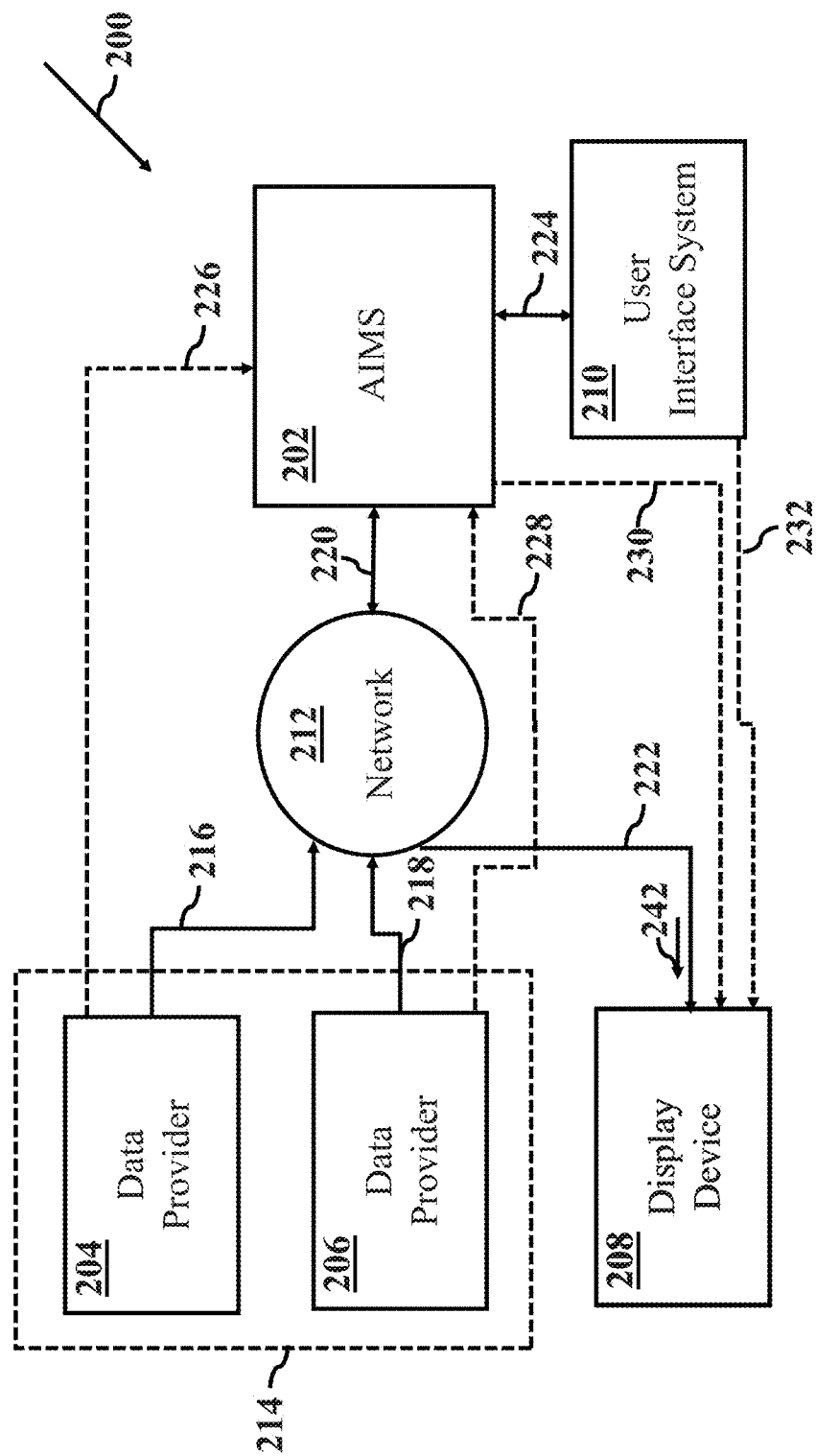

FIGS. 2A-2D illustrate a system 200 for anesthesia information management in accordance with aspects of the present disclosure. The system 200 allows patient laboratory test data to be organized and displayed in a clinically relevant matter to allow interpretation and assessment of patient condition by the anesthesia provider. FIG. 2A illustrates system 200 at a time $t_1$. FIG. 2B illustrates system 200 at a time $t_2$. FIG. 2C illustrates system 200 at a time $t_3$. FIG. 2D illustrates system 200 at a time $t_4$.

As shown in FIG. 2A, system 200 includes an anesthesia information management system (AIMS) component 202, a first data provider 204, a second data provider 206, a display device 208, a user interface (UI) system 210 and a network 212. In some embodiments, the first data provider 204 and the second data provider 206 may be a single entity, as indicated by dashed box 214.

In general, the first data provider 204 and the second data provider 206 may be any device or system that is operable to provide measurement data of one or more parameters associated with a patient, including variety of parameters measured through laboratory tests as described above, other physiological parameters (e.g., blood pressure, heart rate, temperature, blood oxygen saturation, respiratory rate). Non-limiting examples may include a clinical diagnostic device, such as chemistry analyzers, immunoassay analyzers, assay kits and associated instruments, and hematology analyzers, as well as portable instruments and assay kits used at the patient bedside. Alternatively, the data providers 204 and 206 may include monitoring and/or therapeutic devices.

In one example, prior to a surgical procedure, biological samples of a patient is sent to laboratories in order to perform standard tests, where the biological samples may include but not limited to blood, excreta (e.g., urine), other bodily fluid and tissues. The standard tests may be performed by at least one of the first data provider 204 and the second data provider 206. It should also be understood that the first data provider 204 and the second data provider 206 are illustrated merely for purposes of discussion. Any number of data providers may be implemented in accordance with aspects of the present disclosure.

Consider, for example, the case where the testing laboratory tests a blood sample of the patient. The patient laboratory test data may include data associated with at least one of white blood cell count, hemoglobin, platelet count and hematocrit percentage from the blood sample of the patient. For one or more of the parameters, it may be measured at an initial time, and subsequently measured at constant or varying time intervals.

In a non-limiting example embodiment, data provider 204 may provide patient laboratory test data associated with a parameter that is different from the patient laboratory test data as provided by the second data provider 206. For example, the first data provider 204 may provide patient laboratory test data that includes data associated with the white blood cell count from a blood sample of the patient at an initial time, whereas the second data provider 206 may provide patient laboratory test data that includes data associated with the platelet count from the blood sample of the patient at the initial time.

In a non-limiting example embodiment, the first data provider 204 may provide patient laboratory test data associated with the same parameter that is provided from the patient laboratory test data as provided by the second data provider 206, but at different times. For example, data provider 204 may provide patient laboratory test data that includes data associated with the white blood cell count from a blood sample of the patient at an initial time, whereas the second data provider 206 may provide patient laboratory test data that includes data associated with the white cell blood count from a blood sample of the patient at a later time.

In a non-limiting example embodiment, the first data provider 204 may provide patient laboratory test data associated with a parameter that is different from the patient laboratory test data as provided by the second data provider 206, and from different times. For example, the first data provider 204 may provide patient laboratory test data that includes data associated with the white blood cell count from a blood sample of the patient at an initial time, whereas the second data provider 206 may provide patient laboratory test data that includes data associated with the platelet count from a blood sample of the patient at a subsequent time.

The first data provider 204 is arranged and configured to communicate with network 212 via a communication channel 216, whereas the second data provider 206 is arranged and configured to communicate with network 212 via a communication channel 218. In the case where the first data provider 204 and the second data provider 206 may be a single data provider, the single data provider may be arranged and configured to communicate with network 212 via either communication channel 216 or communication channel 218. The first data provider 204 and the second data provider 206 will be described in further detail by way of example below with respect to FIGS. 2B-2D and 4.

The first data provider 204 provides first patient laboratory test data 234 to AIMS component 202 by way of communication channel 216, network 212 and communication channel 220, and the second data provider 206 provide second patient laboratory test data 236 to AIMS component 202 by way of communication channel 218, network 212 and communication channel 220. In accordance with another aspect of the present disclosure, AIMS component 202 may receive additional patient laboratory test data from additional data providers and additional test data from more blood samples at different times.

AIMS component 202 is configured and arranged: to communicate with network 212 via a communication channel 220 and to communicate with UI system 210 via a communication channel 224. In some embodiments, AIMS component 202 may be alternatively arranged and/or configured to communicate directly: with the first data provider 204 via an optional communication channel as indicated by the dashed line 226; with the second data provider 206 via an optional communication channel as indicated by the dashed line 228 and with display device 208 via an optional communication channel as indicated by the dashed line 230.

The display device 208 is configured and arranged to communicate with network 212 via a communication channel 222. Display device 208 may be alternatively arranged to communicate directly with UI system 210 via an optional communication channel as indicated by the dashed line 232.

The display device 208 may include a display, such as a liquid crystal display, a touch screen, a speaker, a printer, and/or hardware and/or software components that are configured to allow the AIMS component 202 to output data.

In this example, AIMS component 202, display device 208 and UI system 210 are illustrated as individual devices. However, in some embodiments, at least two of AIMS component 202, display device 208, and UI system 210 may be combined as a single device.

Further, in some embodiments, at least one of AIMS component 202 and UI system 210 may be implemented as a computer having one or more processors and tangible computer-readable media for carrying or having computer-executable instructions or data structures stored thereon. Such tangible computer-readable media can be any available media that can be accessed by a general-purpose or special-purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general-purpose or special-purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

The one or more processors can be, but are not limited to, a central processing unit (CPU), a hardware microprocessor, a multi-core processor, a single core processor, a field programmable gate array (FPGA), an application-specific integrated circuit (ASIC), a digital signal processor (DSP), or other similar processing device capable of executing any type of instructions, algorithms, or software for controlling the operation of AIMS component 202 and the UI system 210.

Communication channels 216, 218, 220, 222, 224, 226, 228, 230 and 232 may be any known type of communication channel, non-limiting examples of which include wired communication such as coaxial cable and fiber-optic link to allows communication via Ethernet, and the like, wireless communication such as wireless network (IEEE 802.XX) cellular data service (3G/4G/5G), short-range communication technologies (e.g., Bluetooth, RFID, NFC, Zigbee), and the like and combinations thereof of wired communication and wireless communication, which enable transfer of information. However, one of ordinary skill in the art would understand that the communication channels are not limited to these examples, and the communication channels could be implemented by other means within the capabilities of one of ordinary skill in the art.

Figure 3:
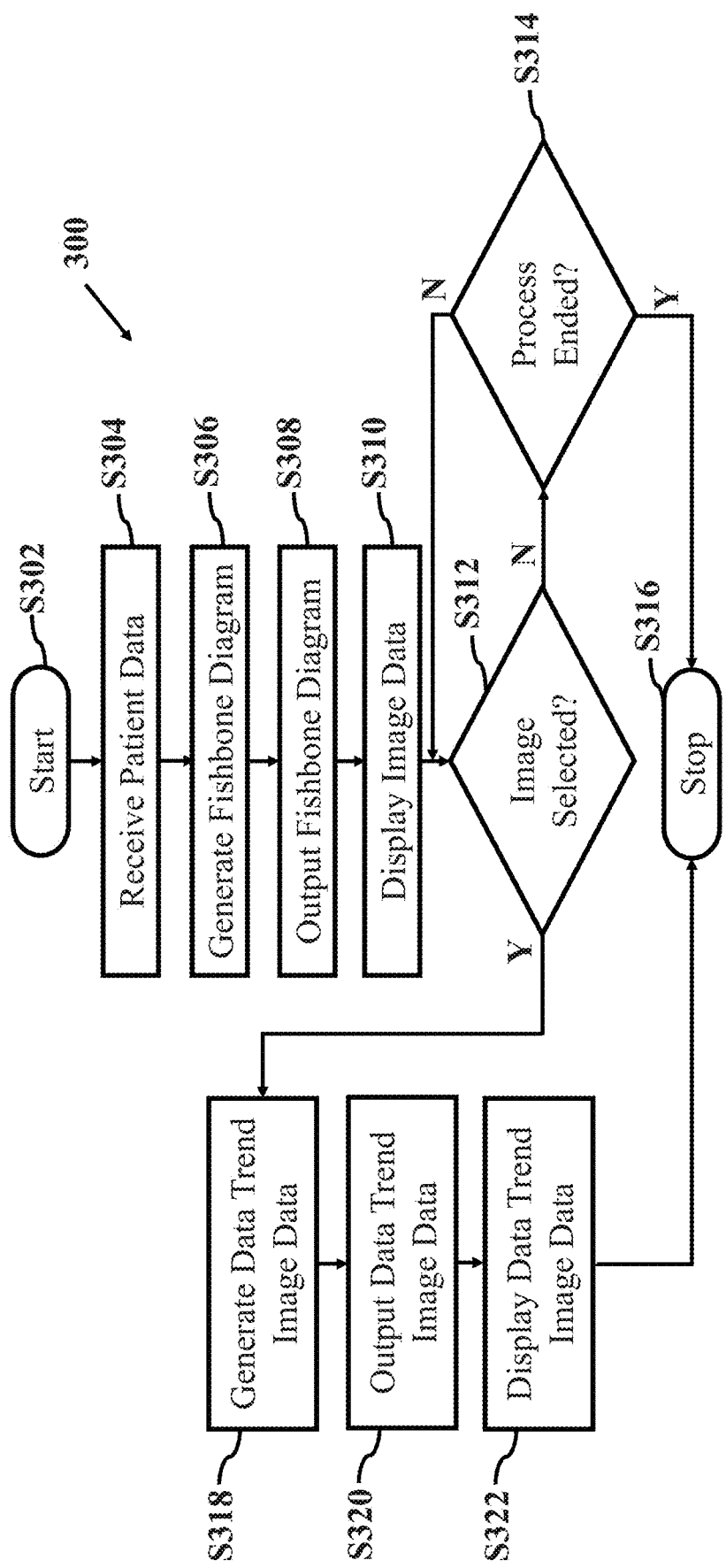
FIG. 3 illustrates an example method for managing anesthesia information in accordance with aspects of the present disclosure.

An example method 300 illustrated in FIG. 3 is provided for managing anesthesia information in accordance with aspects of the present disclosure will now be described with additional reference to FIGS. 4-7E. The method 300 allows the system 200 to organize and display patient laboratory data in a clinically relevant matter to allow interpretation and assessment of patient condition by the anesthesia provider. For purposes of discussion, when describing example method 300, let an anesthesia provider be handling a patient during an acute care preoperative anesthesia process.

As shown in FIG. 3, method 300 starts (S302) and patient data is received (S304). In an example embodiment, the patient data which may include one or more laboratory test results is received by a data input component. The data input component may be in communication with at least one of the first data provider 204 and the second data provider 206. Further, the data input component may be in communication with other devices operable to provide the patient data. This will be described in greater detail with additional reference to FIGS. 2A and 4.

In a non-limiting example embodiment, each of the first data provider 204 and the second data provider 206 takes the form of a respective computer at a respective testing laboratory that is separately located from AIMS component 202, wherein each computer includes at least a memory (not shown) and a communications component (not shown). Each memory has respective patient data stored therein. Each communications component is able to provide the respective patient data from the respective memory to AIMS component 202, either directly or by way of network 212.

In another non-limiting example embodiment, each of the first data provider 204 and the second data provider 206 takes the form of a respective computer at a respective testing laboratory that is separately located from AIMS component 202, wherein each computer includes at least a memory (not shown) that has respective patient data stored therein. A respective user (not shown) of each of the first data provider 204 and the second data provider 206 may be able to access respective patient data stored therein and provide the respective patient data to AIMS component 202, either directly or by way of network 212, by any known manner. Non-limiting examples of ways in which a user may provide the patient data to AIMS component 202 include via email, via telephone, or by physically transporting a storage media having the patient data transferred thereon.

In another non-limiting example embodiment, each of the first data provider 204 and the second data provider 206 takes the form of a respective computer at a respective testing laboratory that is co-located with AIMS component 202, wherein each computer includes at least a memory (not shown) and a communications component (not shown). Each memory has respective patient data stored therein. Each communications component is able to provide respective patient data directly from the respective memory to AIMS component 202.

In another non-limiting example embodiment, each of the first data provider 204 and the second data provider 206 takes the form of a respective computer at a respective testing laboratory that co-located with AIMS component 202, wherein each computer includes at least a memory (not shown) that has patient data stored therein. A respective user (not shown) of each of the first data provider 204 and the second data provider 206 may be able to access respective patient data stored therein and provide the respective patient data directly to AIMS component 202.

In general, AIMS component 202 may receive patient laboratory test data of a particular patient from any number of different data providers, wherein each data provider may provide patient laboratory test data associated with any one of a specific measurable parameter, a specific time for which the patient laboratory test data of a specific measurable parameter was obtained, or a plurality of measurable parameters associated with a single physiological sample of the patient.

Network 212 may be any known communication network including a wireless network, a wired network, a public switched telephone network (PSTN), the Internet and combinations thereof.

When communicating by way of network 212, AIMS component 202 may perform such functions as link layer and physical layer outroute coding and modulation (e.g., DVB-S2 adaptive coding and modulation), link layer and physical layer inroute handling (e.g., IPOS), inroute bandwidth allocation and load balancing, outroute prioritization, web acceleration and HTTP compression, flow control, encryption, redundancy switchovers, traffic restriction policy enforcement, data compression, TCP performance enhancements (e.g., TCP performance-enhancing proxies, such as TCP spoofing), quality of service functions (e.g., classification, prioritization, differentiation, random early detection (RED), TCP/UDP flow control), bandwidth usage policing, dynamic load balancing, and routing.

When either or both of the first data provider 204 or the second data provider 206 provide patient laboratory test data to AIMS component 202, AIMS component 202 receives the patient laboratory test data. This will be described in greater detail with reference to FIG. 4.

Figure 4:
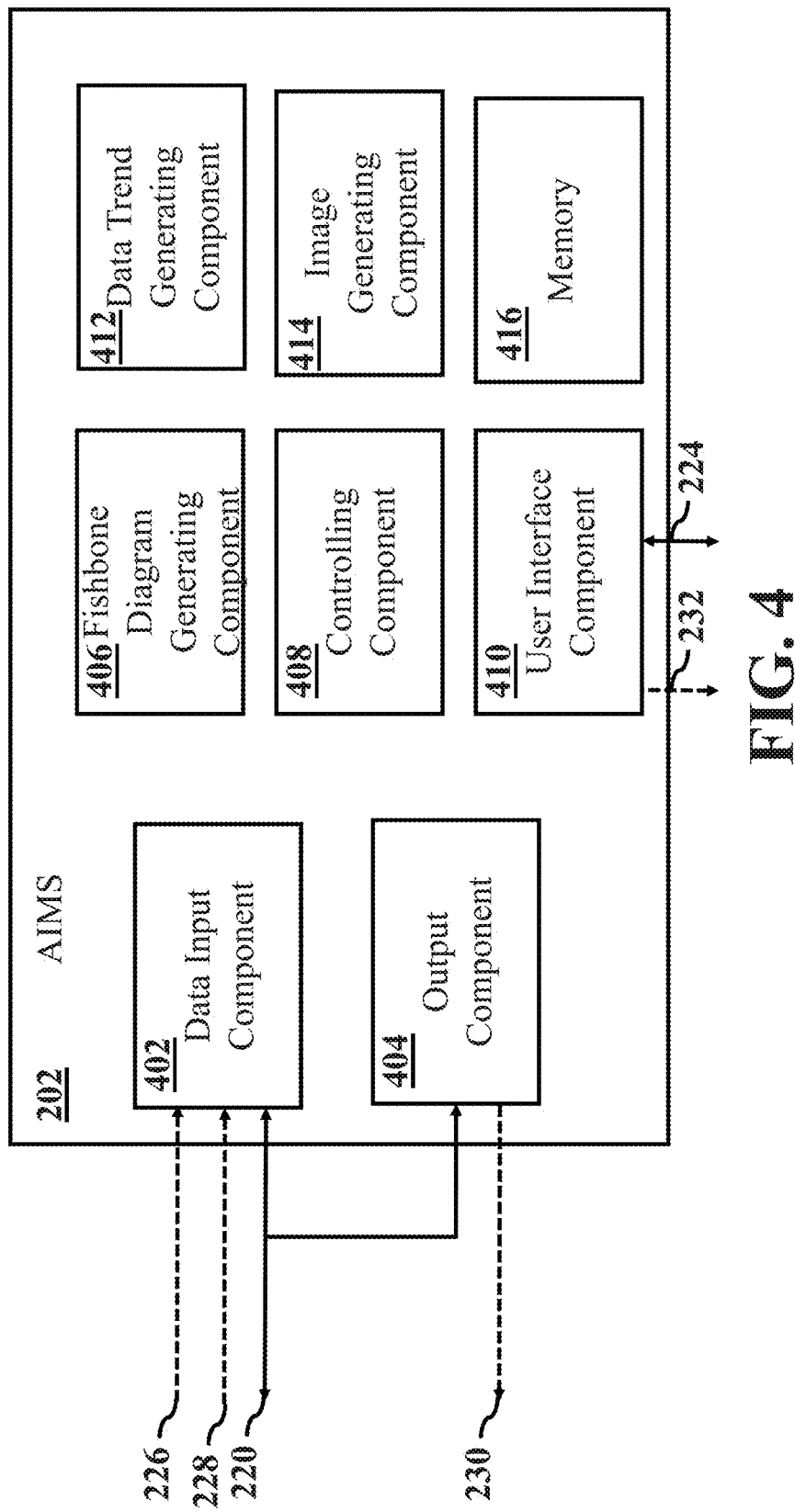
FIG. 4. illustrates a block diagram of an anesthesia information management system (AIMS) component of the system of FIG. 2.

FIG. 4. illustrates a block diagram of AIMS component 202 of system 200 of FIG. 2. The constituent components of AIMS component 202 process data received from the first data provider 204 and the second data provider 206 in order to allow the system 200 to organize and display patient laboratory data in a clinically relevant matter for interpretation and assessment of patient condition by the anesthesia provider.

As shown in FIG. 4, AIMS component 202 includes a data input component 402, an output component 404, a fishbone diagram generating component 406, a controlling component 408, a user interface (UI) component 410, a data trend generating component 412, an image generating component 414 and a memory 416. A general description of the configuration of each of the components is provided below, and further details of the operation of the components of the AIMS component 202 are described later in detail with reference to FIGS. 2A and 3.

Data input component 402 is configured and arranged to communicate with network 212 via communication channel 220. Further, data input component 402 may optionally be configured and arranged to communicate directly with the first data provider 204 via communication channel 226 and to communicate directly with the second data provider 206 via communication channel 228.

Output component 404 is additionally configured and arranged to communicate with network 212 via communication channel 220. Further, output component 404 may optionally be configured and arranged to communicate directly with display device 208 via communication channel 230.

UI component 410 is configured and arranged to communicate with UI system 210 via communication channel 224. In an optional embodiment wherein UI system 210 and AIMS component 202 are a single device, UI component 410 may be configured and arranged to communicate directly with display device 208 via communication channel 232.

In this example, data input component 402, output component 404, fishbone diagram generating component 406, controlling component 408, UI component 410, data trend generating component 412, image generating component 414 and memory 416 are illustrated as individual devices. However, in some embodiments, at least two of data input component 402, output component 404, fishbone diagram generating component 406, controlling component 408, UI component 410, data trend generating component 412, image generating component 414 and memory 416 may be combined as a single device.

Further, in some embodiments, at least one of data input component 402, output component 404, fishbone diagram generating component 406, controlling component 408, UI component 410, data trend generating component 412, image generating component 414 and memory 416 may be implemented as a computer having one or more processors and tangible computer-readable media for carrying or having computer-executable instructions or data structures stored thereon. Such tangible computer-readable media can be any available media that can be accessed by a general-purpose or special-purpose computer. The one or more processors can be, but are not limited to, a central processing unit (CPU), a hardware microprocessor, a multi-core processor, a single core processor, a field programmable gate array (FPGA), an application specific integrated circuit (ASIC), a digital signal processor (DSP), or other similar processing device capable of executing any type of instructions, algorithms, or software for controlling the operation of AIMS component 202 and the constituent components thereof.

Example tangible computer-readable media may be coupled to a processor such that the processor may read information from, and write information to, the tangible computer-readable media. In the alternative, the tangible computer-readable media may be integral to the processor. The processor and the tangible computer-readable media may reside in an application-specific integrated circuit (ASIC). In the alternative, the processor and the tangible computer-readable media may reside as discrete components.

Non-limiting example systems include a computer system/server, which is operational with numerous other general purpose or special purpose computing system environments or configurations. Examples of well-known computing systems, environments, and/or configurations that may be suitable for use with the computer system/server include, but are not limited to, personal computer systems, server computer systems, thin clients, thick clients, handheld or laptop devices, multiprocessor systems, microprocessor-based systems, STBs, programmable consumer electronics, network PCs, minicomputer systems, mainframe computer systems, and distributed cloud computing environments that include any of the above systems or devices, and the like.

Such a computer system/server may be described in the general context of computer system-executable instructions, such as program modules, being executed by a computer system. Generally, program modules may include routines, programs, objects, components, logic, data structures, and so on that perform particular tasks or implement particular abstract data types. Further, such a computer system/server may be practiced in distributed cloud computing environments where tasks are performed by remote processing devices that are linked through a communications network. In a distributed cloud computing environment, program modules may be located in both local and remote computer system storage media including memory storage devices.

Components of an example computer system/server may include, but are not limited to, one or more processors or processing units, a system memory, and a bus that couples various system components including the system memory to the processor.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A program/utility, having a set (at least one) of program modules, may be stored in the memory by way of example, and not limitation, as well as an operating system, one or more application programs, other program modules, and program data. Each of the operating systems, one or more application programs, other program modules, and program data or some combination thereof, may include an implementation of a networking environment. The program modules generally carry out the functions and/or methodologies of various embodiments of the application as described herein.

Data input component 402 may be any device or system that is operable to: receive input data including first patient laboratory test data and second patient laboratory test data; and in cases where the first data provider 204 and the second data provider 206 are a single data provider 214, receive the first patient laboratory test data from the first data provider 204 and receive the second patient laboratory test data from data provider 214.

In cases where the first data provider 204 provides the patient laboratory test data directly to data input component 402, the patient laboratory test data is received via communication channel 226. In cases where the second data provider 206 provides the patient laboratory test data directly to data input component 402, the patient laboratory test data is received via communication channel 226.

Controlling component 408 may be any device or system that is operable to control the operation of data input component 402, output component 404, fishbone diagram generating component 406, user interface (UI) component 410, data trend generating component 412 and memory 416.

Memory 416 may be any device or system that is operable to store and manage data received by the first data provider 204 or the second data provider 206, to store and manage data generated by fishbone diagram generating component 406, user interface component 410 and data trend generating component 412 and to store and manage desired program code means in the form of computer-executable instructions or data structures and which can be accessed by a general purpose or special purpose computer. Non-limiting examples of memory 416 include any known physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general-purpose or special-purpose computer.

Returning to FIG. 4, input component 402 provides the received first patient laboratory test data 234 and second patient laboratory test data 236 to memory 416 for storage.

Returning to FIG. 3, after the patient data is received (S304), a fishbone diagram is generated (S306). In an example embodiment, fishbone diagram generating component 406 generates a fishbone diagram.

For example, as shown in FIG. 4, controlling component 408 instructs fishbone diagram generating component 406 to retrieve first patient laboratory test data 234 and second patient laboratory test data 236 from memory 416 and to generate a fishbone diagram for each of the retrieved first patient laboratory test data 234 and second patient laboratory test data 236.

Fishbone diagram generating component 406 may be any device or system that is operable to: generate fishbone diagram image data associated with patient laboratory test data so as to include a most recently received value of a measurable parameter; and to generate the fishbone diagram image data associated with the patient laboratory test data so as to further include a time associated with a most recently received value of the measurable parameter and a unit of measure of the measurable parameter.

Fishbone diagram generating component 406 then retrieves first patient laboratory test data 234 and second patient laboratory test data 236 from memory 416 and generates fishbone diagram image data for each of the retrieved first patient laboratory test data 234 and second patient laboratory test data 236.

As discussed above with reference to FIG. 1, the fishbone diagram image data includes the data associated with the most recent values of the measurable parameters of the patient. Accordingly, although first patient laboratory test data 234 may include a plurality of values of a measurable parameter, wherein each value corresponds to a time at which the parameter was measured, fishbone diagram generating component 406 generates the fishbone diagram image data associated with first patient laboratory test data 234 to include the most recent value of the measurable parameter. Similarly, although second patient laboratory test data 236 may include a plurality of values of a second measurable parameter, wherein each value corresponds to a time at which the second parameter was measured, fishbone diagram generating component 406 generates the fishbone diagram image data associated with second patient laboratory test data 236 to include the most recent value of the second measurable parameter.

It should be understood that the present disclosure is not limited to a display in which a displayed fishbone diagram will include the most recent value of the measurable parameters. For example, the displayed diagram is not limited to a fishbone shape and may be a non-fishbone diagram.

Additionally, although in the embodiment of the present disclosure described above, the displayed fishbone or non-fishbone diagram displays on the most recent value of the measurable value, the present disclosure is not limited to such a display. In another embodiment, the fishbone or non-fishbone diagram may display a historical value of the measurable parameter in addition to or instead of the most recent value of the measurable parameter. For example, the displayed diagram including coagulation parameters may include a most recent value of prothrombin time (PT) of 25 seconds measured at 11:14 AM, as well as a historical value of 20 seconds measured at 10:45 AM. Further, each measurement value may be associated in the displayed diagram with corresponding measurement time.

In an example embodiment of the present disclosure, fishbone diagram generating component 406 generates a fishbone diagram when provided to a display device, wherein the displayed fishbone diagram will have a predetermined form based on the type of patient laboratory test data. Non-limiting examples of forms include predetermined fishbone diagrams, a complete blood count (CBC) form—such as illustrated above with reference to FIG. 1, a coagulation studies form, a chemistry form and a listing form. The listing form may not include an actual fishbone diagram, but merely lists distinct data fields, such as for example a blood gas form.

Fishbone diagram generating component 406 then stores the generated fishbone diagram image data for each of the retrieved first patient laboratory test data 234 and second patient laboratory test data 236 into memory 416.

Returning to FIG. 3, after the fishbone diagram is generated (S306), the fishbone diagram is outputted (S308). In an example embodiment, output component 404 outputs the fishbone diagram.

For example, as shown in FIG. 4, controlling component 408 instructs image generating component 414 to retrieve fishbone diagram image data for each of the retrieved first patient laboratory test data 234 and second patient laboratory test data 236 from memory 416 and to retrieve first patient laboratory test data 234 and second patient laboratory test data 236.

Image generating component 414 may be any device or system that is able to generate initial image display data that includes fishbone diagram image data and laboratory test data, to generate enhanced image display data that includes data trend image data and to generate combination image display data that includes combinations of fishbone diagram image data, laboratory test data and data trend image data, wherein the initial image display data may be displayed on a display device as an initial image display that includes a fishbone diagram image and an image of laboratory test data, wherein the enhanced image display data may be displayed on a display device as an enhanced image display that includes a data trend image of a data trend associated with the fishbone diagram, and wherein the combination image display data may be displayed on a display device as a combination image display that includes a combination of the fishbone diagram image, the image of laboratory test data and the data trend image.

In an example embodiment, image generating component 414 may generate image data associated with the laboratory test data as table image data to be displayed as a table image by a display device, wherein the table image includes table information and second table information, wherein the first table information corresponds to the first patient laboratory test data and wherein the second table information corresponds to the second patient laboratory test data. Still further, in other embodiments, image generating component 414 may generate image data associated with the laboratory test data as table image data to be displayed as a table image by a display device, wherein the table image further includes additional table information corresponding to additional patient laboratory test data.

Image generating component 414 then generates the image data to be output by output component 404. For purposes of discussion, let image generating component 414 generate the image data to be output by output component 404 as initial image display data.

Controlling component 408 then instructs image generating component 414 to provide the initial image display data to output component 404.

Output component 404 may be any device or system, as will be described in more detail below, that is operable to: output a fishbone diagram image data to display device 208 to be displayed as image data so as to include a first fishbone diagram section and a second fishbone diagram section, wherein the first fishbone diagram section corresponds to first patient laboratory test data and wherein the second fishbone diagram section corresponds to second patient laboratory test data; output data trend image data to display device 208 to be displayed as image data so as to include a first graphical function and a second graphical function, wherein the first graphical function corresponds to the first patient laboratory test data and wherein the second graphical function corresponds to the second patient laboratory test data based on a selection of first image data; to output table image data to display device 208 to be displayed as image data so as to further include a table including first table information and second table information, wherein the first table information corresponds to the first patient laboratory test data and wherein the second table information corresponds to the second patient laboratory test data; and to output the table image data to display device 208 to be displayed as image data so as to further include additional table information corresponding to additional patient laboratory test data.

Output component 404 then provides the fishbone diagram image data for each of the retrieved first patient laboratory test data 234 and second patient laboratory test data 236 to display device 208 by way of communication channel 220. In other words, as shown in FIG. 2B, AIMS component 202 provides the initial image display data 238 to display device 208 by way of communication channel 220, network 212 and communication channel 222.

Returning to FIG. 3, after the fishbone diagram is outputted (S308), image data is displayed (S310). In an example embodiment, display device 208 displays the initial image display data as a combination of fishbone diagram images and an image of the laboratory test data. In this example embodiment, the combination includes the fishbone diagram image associated with the retrieved first patient laboratory test data 234, the fishbone diagram image associated with the second patient laboratory test data 236 and a table image associated with the laboratory test data. The combination of fishbone diagram images and an image of the laboratory test data will be described in greater detail with reference to FIG. 5.

FIG. 5 illustrates an example initial image display 500 in accordance with an aspect of the present disclosure. By providing the initial image display 500, an anesthesia provider can easily see, not only all the most current data of all the lab results for the patient, but also all the previous values of the lab results for the patient on one single image.

As shown in the figure, initial image display 500 include a display section 502 and a display section 504. Display section 502 includes a plurality of lab panels, non-limiting examples of which are shown and labeled as lab panel 506, lab panel 508, lab panel 510, lab panel 512, lab panel 514 and lab panel 516. Display section 504 includes a lab data table 518, which a plurality of rows in the y-axis 520 and a plurality of columns in the x-axis 522.

Display section 502 displays patient laboratory test data associated with a patient in related groupings as distinct lab panels. It should be noted that display section 502 is a non-limiting example that includes six example lab panels. In other example embodiments, any number of different lab panels may be included in display section 502.

Display section 502 includes the fishbone diagram image data for each of the retrieved first patient laboratory test data 234 and second patient laboratory test data 236 as provided by AIMS component 202. In one embodiment of the present disclosure, the displayed fishbone diagram will have at least one of a most recent value and a historical value of the measurable parameter.

Lab panel 506 includes the most recent patient laboratory test data associated with the complete blood count of the patient. In this example embodiment, lab panel 506 includes the most recent patient laboratory test data associated with the white blood cell count (WBC), the hemoglobin (Hgb), the platelets (Plt) and the hematocrit (Hct) of the blood of the patient. Lab panel 506 displays the most recently received value for each test, along with the time for which the value is received and the units of measure for that particular test.

Lab panel 508 includes the most recent laboratory test data associated with coagulation studies of the blood of the patient. In this example embodiment, lab panel 508 includes the most recent patient laboratory test data associated with the prothrombin time (PT), the partial thromboplastin time (PTT) and the international normalized ratio (INR) of the blood of the patient. Lab panel 508 displays the most recently received value for each test, along with the time for which the value is received and the units of measure for that particular test.

Lab panel 510 includes the most recent patient laboratory test data associated with the chemistry of the blood of the patient. In this example embodiment, lab panel 510 includes the most recent patient laboratory test data associated with the sodium (Na), the chlorine (Cl), the blood urea nitrogen (Bun), the glucose, the creatinine (Creat) and the carbon dioxide (CO2) of the blood of the patient. Lab panel 510 displays the most recently received value for each test, along with the time for which the value is received and the units of measure for that particular test.

Lab panel 512 includes the most recent patient laboratory test data associated with the blood gas of the blood of the patient. In this example embodiment, lab panel 512 includes the most recent patient laboratory test data associated with the pH, the partial pressure of carbon dioxide ($pCO_2$), the partial pressure of oxygen ($pO_2$), the bicarbonate ($HCO_3$), the based excess (BE) and the oxygen saturation (Sao2) of the blood of the patient. Lab panel 512 displays the most recently received value for each test, along with the time for which the value is received and the units of measure for that particular test.

Lab panel 514 includes the most recent patient laboratory test data associated with the liver function tests as determined from the blood of the patient. In this example embodiment, lab panel 512 includes the most recent patient laboratory test data associated with the serum albumin test (Alb), the aspartate aminotransferase test (AST), the alanine aminotransferase test (ALT), the alkaline phosphatase test (Alk Phos), the total bilirubin test (T. Bili), the calcium (Ca) and the magnesium (Mg) as determined from the blood of the patient. Lab panel 514 displays the most recently received value for each test, along with the time for which the value is received and the units of measure for that particular test.

Lab panel 516 is reserved from the most recent patient laboratory test data associated with other miscellaneous aspects of the blood of the patient that may be added. Lab panel 516 will be able to display the most recently received value for each test, along with the time for which the value would be received and the units of measure for that particular test.

It should be noted that other lab panels may include patient laboratory test data associated with other measurable parameters of the patient, such as for example, those associated with urine of the patient.

Display section 504 includes first patient laboratory test data 234 and second patient laboratory test data 236 as provided by AIMS component 202. Again, as noted above, first patient laboratory test data 234 and second patient laboratory test data 236 includes all values of the measurable parameter.

Lab data table 518 in display section 504 provides historical data of measurable parameters of the patient. Y-axis 520 displays the time when a result was received and x-axis 522 provides the list of available laboratory test results. In contrast with the lab panels in display section 502, which display the most recent patient laboratory test data for any particular measurable parameter of the patient, lab data table 518 provides all the data for all recorded times of the measurable parameters of the patient. As a non-limiting example, lab data table 518 includes an entry 524 that indicated that the blood of the patient at 7:00 AM has an INR of 1.5, as compared with the INR of 4.0 as listed in lab panel 508 of display section 502. It should be understood that the positions of the diagrams and the historical table in the image display as disclosed herein are for exemplary purposes and are not meant to limit the scope of the present disclosure to any particular embodiment. The diagrams and historical table may be positioned as needed within the image display.

Further, lab data table 518 may additionally include additional patient laboratory test data that is not included in any of the panels in display section 502.

As noted above, with initial image display 500, an anesthesia provider can easily see, not only all the most current data of all the lab results for the patient, but also all the previous values of the lab results for the patient on one single image.

Returning to FIG. 3, after the image data is displayed (S310), it is determined whether an image is selected (S312). In an example embodiment, user interface system 210 enables selection of image data.

For example, consider the situation where an anesthesia provider desires to view trend data associated with coagulation studies of the patient. In particular, presume that the anesthesia provider desires to see more than the most recent values of the parameters associated with the coagulation studies of the patient as provided by lab panel 508, as shown in FIG. 5. Further, presume that the anesthesia provider desires to see more than the stand-alone historical values of the parameters associated with the coagulation studies of the patient as provided by display section 504, as shown in FIG. 5.

In accordance with aspects of the present disclosure, the anesthesia provider may select lab panel 508, by any known manner, wherein the selection will provide the anesthesia with an image of trends of the data of the parameters associated with the coagulation studies of the patient.

As shown in FIG. 2C, UI system 210 provides a selection instruction 240 to AIMS component 202 by way of communication channel 224. Selection instruction 240 informs AIMS component 202 that a lab panel on display 500 has been selected such that enhanced image display data is now desired, by the anesthesia provider, to be displayed as an enhanced image on display device 208.

UI system 210 may be any device or system that is operable to enable selection of image data. UI system 210 may include one or more layers including a human-machine interface (HMI) machines with physical input hardware such keyboards, mice, game pads and output hardware such as computer monitors, speakers, and printers. Additional UI layers in UI component 410 may interact with one or more human senses, including: tactile UI (touch), visual UI (sight), and auditory UI (sound).

In this example embodiment, UI system 210 may enable an anesthesia provider to select a lab panel that is displayed on display device 208.

As mentioned above, in some embodiments, at least two of AIMS component 202, display device 208 and UI system 201 may be combined as a single device. For purposes of discussion, let display device 208, UI system 210 and UI component 410 of AIMS component 202 be distinct devices. Accordingly, UI system 210 may communicate with display device 208, for example via communication channel 232, so as to enable the anesthesia provider to move an image of a cursor over initial image display 500 of FIG. 5 to select a lab panel.

If a lab panel within initial image display 500 is selected, display device provides identifying information to identify the lab panel that has been selected back to UI system 210 via communication channel 232. UI system 210 then provides selection instruction 240 to AIMS component 202.

Returning to FIG. 4, selection instruction 240 identifies the lab panel selected by the anesthesia provider such that the data trend image data associated with the selected lab panel may be retrieved from memory 416. User interface component 410 receives selection instruction 240.

UI component 410 may be any device or system that is operable to: generate a trends diagram instruction based on user interface instructions; and enable selection of image data. UI component 410 may include one or more layers including a human-machine interface (HMI) machines with physical input hardware such as keyboards, mice, game pads and output hardware such as computer monitors, speakers, and printers. Additional UI layers in UI component 410 may interact with one or more human senses, including tactile UI (touch), visual UI (sight), and auditory UI (sound).

UI component 410 then provides selection instruction for controlling component 408. Controlling component 408 determines whether an image has been selected based on receipt of the selection instruction 240.

Returning to FIG. 3, if it is determined that an image is not selected (No at S312), then it is determined whether the process has ended (S314). For example, as shown in FIG. 4, if controlling component 408 does not receive a selection instruction 240, then an image has not been selected. In such a situation, controlling component 408 continues to wait for a selection instruction 240 until the process ends. The process is a process associated with the monitoring of the patient, which may include any of a preoperative, operative and perioperative care process. In an example embodiment, the process may be determined to have ended after a predetermined period of time. In other example embodiments, the process may be determined to have ended when power to AIMS component 202 is discontinued.

Returning to FIG. 3, if it is determined that the process has ended (Yes at S314), then method 300 stops (S316).

However, if it is determined that the process has not ended (No at S314), then the system waits for an image to be selected (return to S312). If it is determined that an image is selected (Yes at S312), then data trend image data is generated (S318). In an example embodiment, data trend generating component 412, generates data trend image data based on the trends diagram instruction, wherein the data trend image data is based on the patient laboratory test data.

For example, as shown in FIG. 4, data trend generating component 412 may be any device or system that is operable to, as will be described in greater detail below: generate data trend image data based on a trends diagram instruction, wherein the data trend image data is based on patient laboratory test data.

In an example embodiment, when a user clicks within one of the lab panels within display section 502 of initial image display 500 as shown in FIG. 5, a graphic representation of data trends over time for each test grouping may be displayed. As shown in FIG. 4, data trend generating component 412 will generate data trend image data, which will then be provided to image generating component 414.

Image generating component 414 then uses the data trend image data to generate enhanced image display data, such that a display device may generate an enhanced image display as a graphic representation of data trends over time for each test grouping. This will be described in greater detail with reference to FIGS. 6A-B.

Figure 6A:
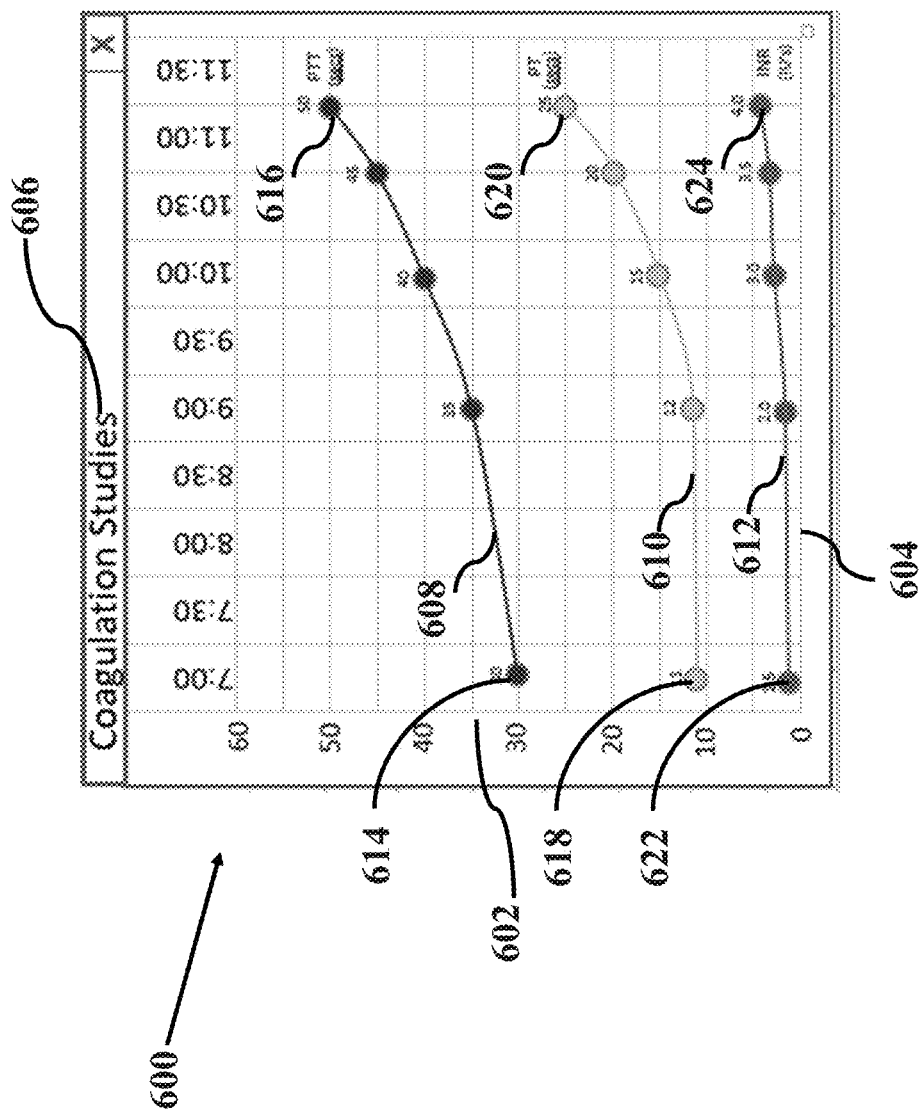
Figure 6B:
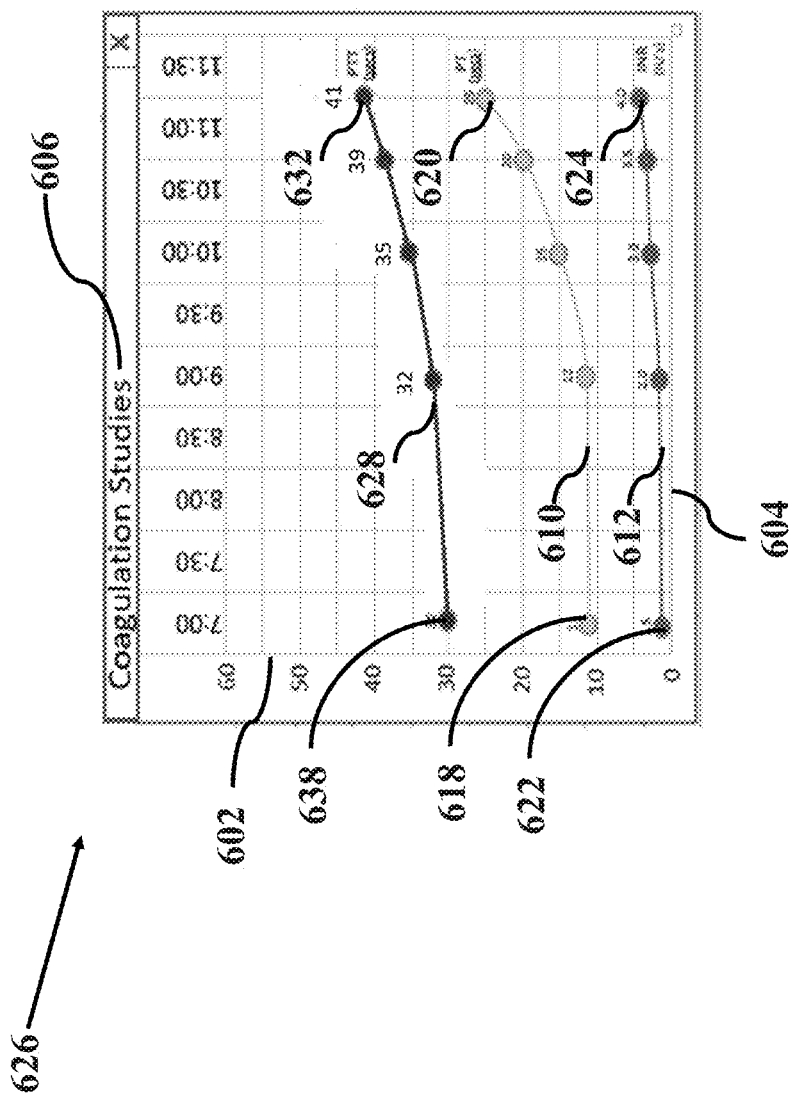

FIGS. 6A-B illustrate example data trend images in accordance with aspects of the present disclosure. FIG. 6A illustrates an example data trend image 600, whereas FIG. 6B illustrates another example data trend image 626. The exemplary data trend images illustrated in FIGS. 6A-B provide a way for an anesthesia provider to easily view a trend of measurable parameter data in order to determine if a modified anesthesia service is required.

As shown in FIG. 6A, data trend image 600 includes a y-axis 602, an x-axis 604, a title 606, a function 608, a function 610 and a function 612. Function 608 comprises a plurality of data points connected by interpolating connecting lines, wherein the plurality of data points include an initial data point 614 and a most recently received data point 616. Function 610 comprises a plurality of data points connected by interpolating connecting lines, wherein the plurality of data points include an initial data point 618 and a most recently received data point 620. Function 612 comprises a plurality of data points connected by interpolating connecting lines, wherein the plurality of data points include an initial data point 622 and a most recently received data point 624.

In this example embodiment, function 608 corresponds to a first patient laboratory test data corresponding to a first measurable parameter of the patient. For purposes of discussion, let function 608 correspond to the measured PTT of the patient. As such, initial data point 614 corresponds to the first measured PTT provided at 7:00, whereas most recently received data point 616 corresponds to the most recently measured PTT provided at 11:15.

In this example embodiment, function 610 corresponds to a second patient laboratory test data corresponding to a second measurable parameter of the patient. For purposes of discussion, let function 610 correspond to the measured PT of the patient. As such, initial data point 618 corresponds to the first measured PT provided at 7:00, whereas most recently received data point 620 corresponds to the most recently measured PT provided at 11:15.

In this example embodiment, function 612 corresponds to a third patient laboratory test data corresponding to a third measurable parameter of the patient. For purposes of discussion, let function 612 correspond to the measured INR of the patient. As such, initial data point 622 corresponds to the first measured INR provided at 7:00, whereas most recently received data point 624 corresponds to the most recently measured INR provided at 11:15.

In this example, the data points for the PT, the PTT and the INR are provided at the same respective times. However, it should be noted than in other examples, the data points for each laboratory test data of each measurable parameter may have unrelated times. Unrelated sampling times may indicate that measured parameters were measured at different times, at different laboratories or with different patient samples.

Further, it should be noted that the data of functions 608, 610 and 612 may be provided from a single data provider. In other embodiments, at least one of the data of functions 608, 610 and 612 may be provided by a different data provider.

Further, it should be noted that the data values of any one of functions 608, 610 and 612 may be provided from a single data provider. In other embodiments, at least one of the data from any one of data of functions 608, 610 and 612 may be provided by different data providers.

As previously noted, the data trend may display parameters from the same grouping or different groupings of laboratory tests. Accordingly, at least one of the values, unit and scales may have different configuration settings for different parameters, that is, at least one of the corresponding graphic representation of data trends with respect to values, unit and scales may vary for different parameters. For example, with reference to FIG. 6A, the data points 614 of partial thromboplastin time (PTT) may have a different color code from data point 618 of prothrombin time (PT) and data point 622 of the international normalized ratio (INR). Alternatively, the data points may have different formats and/or shapes, and the data functions 608, 610 and 612 may have different configurations with respect to colors, width, dash types, etc.

In this example, the PT, the PTT and the INR have different units of measure. Accordingly, in order to use a single common y-axis 602 to display functions 608, 610 and 612, the units for each function may be illustrated next to the respective functions. However, the units of each function may be adjusted by appropriate factors of 10 so as to use y-axis 602, which in this example ranges from a value of 0-60.

With data trend image 600, an anesthesia provider can see the most recent received values of patient laboratory test data for a plurality of measurable parameters, as which may have been provided by a fishbone diagram. Further with data trend image 600, an anesthesia provider can see all the historical received values of patient laboratory test data for a plurality of measurable parameters, which may have been provided by prior art methods by way of individual papers or charts. However, in accordance with aspects of the present disclosure, data trend image 600 permits the anesthesia provider to view the combination of the most recent received values of patient laboratory test data for a plurality of measurable parameters and all the historical received values of patient laboratory test data for a plurality of measurable parameters. More importantly, data trend image 600 permits the anesthesia provider to view trends in the patient laboratory test data.

In particular, data trend image 600 permits an anesthesia provider to see a trend of data for an individual set of patient laboratory test data of a single parameter. For example, the anesthesia provider may see that the measured PTT of the patient, as shown by function 608, is not only increasing with time, but the rate of increase is increasing with time. Such a rate of increase might not be readily apparent to the provider by merely viewing the stand-alone values in a table form, for example as shown in display section 504 of FIG. 5.

Further, returning to FIG. 6A, data trend image 600 permits an anesthesia provider to see a relation of trends of data between multiple individual sets of patient laboratory test data of multiple parameters. For example, the anesthesia provider may see that the measured PTT of the patient, as shown by function 608, is increasing with time and that the measured PT of the patient, as shown by function 610, is additionally increasing with time. Still further, the anesthesia provider may see that the rate measured PTT of the patient, as shown by function 608, is increasing with time in a manner that is similar to the rate at which the measured PT of the patient, as shown by function 610, is additionally increasing with time. Such relative rates of different sets of laboratory test data for respective different measured parameters might not be readily apparent to the provider by merely viewing the stand-alone values in a table form, for example as shown in display section 504 of FIG. 5.

Furthermore, the anesthesia provider may click on a plurality of diagrams, with each providing a corresponding graphic representation of data trend over time. The anesthesia provider may configure the positions of the plurality of trend graphs to be displayed side-by-side or as desired. As such, the anesthesia provider may simultaneously view a plurality of trend graphs corresponding to the parameters of different groupings of laboratory tests. Alternatively, the anesthesia provider may overlap a plurality of graphic representations to compare and analyze the correlation among different parameters over a period of time, which will be described further in FIG. 6D and FIG. 6E.

As shown in FIG. 6B, data trend image 626 includes y-axis 602, x-axis 604, title 606, a function 628, function 610 and function 612. Function 628 comprises a plurality of data points connected by interpolating connecting lines, wherein the plurality of data points include an initial data point 638 and a most recently received data point 632.

In this example embodiment, function 628 corresponds to a first patient laboratory test data corresponding to a first measurable parameter of the patient. For purposes of discussion, let function 628 correspond to the measured PTT of the patient. As such, initial data point 638 corresponds to the first measured PTT provided at 7:00, whereas most recently received data point 632 corresponds to the most recently measured PTT provided at 11:15.

The difference between the example embodiment of FIG. 6A and the example embodiment of FIG. 6B is the measured PTT function of the patient.

In the example embodiment of FIG. 6A, the patient has: an initial measured PTT of 30 seconds as measured at 7:15; a second measured PTT of 35 seconds as measured at 9:15; a third measured PTT of 40 seconds as measured at 10:15; a fourth measured PTT of 45 seconds as measured at 11:00; and a most recently measured PTT of 50 seconds as measured at 11:30.

With reference to the exemplary embodiment of FIG. 6A, the patient was supposed to receive an anticoagulant, such as heparin, in order to place the patient's PTT in a therapeutic range prior to surgery. Further, in this example for purposes of discussion, let the patient's PTT therapeutic range be between 45 and 55 seconds.

In the example embodiment of FIG. 6B, the patient has: an initial measured PTT of 30 seconds as measured at 7:15; a second measured PTT of 32 seconds as measured at 9:15; a third measured PTT of 35 seconds as measured at 10:15; a fourth measured PTT of 39 seconds as measured at 11:00; and a most recently measured PTT of 41 seconds as measured at 11:30.

For purposes of discussion, suppose that the example embodiment of FIG. 6B describes a different situation where the patient was supposed to receive an anticoagulant, such as heparin, in order to place the patient's PTT in a therapeutic range prior to surgery. Again, in this example for purposes of discussion, let the patient's PTT therapeutic range be between 45 and 55 seconds. In contrast with the situation discussed above with reference to FIG. 6A, in this example, the patient's PTT is not in a therapeutic range of 45-55 seconds at 11:30. Further, by viewing the trend of function 628, the anesthesia provider may be able to notice that at the low rate of increase, i.e., the changing slope of function 628, that the patient's PTT might not be in a therapeutic range in time for the surgery. In such a case, additional steps might be taken to place to the patient's PTT in the therapeutic range in time for the surgery. Still further, the anesthesia provider may be able to modify the anticipated anesthesia cervices during the surgery based on the additional steps that will be taken to place the patient's PTT in the therapeutic range.

Returning to FIG. 3, after the data trend image data is generated (S318), the data trend image data is outputted (S320).

For example, as shown in FIG. 4, image generating component 414 provides the enhanced image display data to output component 404. In an example embodiment, for example as shown in FIG. 2D, output component 404 outputs the enhanced image display data 242 to the display device by way of communication channel 220, network 212 and communication channel 222.

Returning to FIG. 3, after the data trend image data is outputted (S320), the data trend image data is displayed (S322). For example, as shown in FIG. 2D, display device 208 displays the data trend image data.

In an example embodiment, display device 208 displays the enhanced image display data as combination image display which includes a combination of initial image display 500 as shown in FIG. 5 and a data trend image of a selected lab panel, such as for example data trend image 600 as shown in FIG. 6.

In some embodiments, the enhanced image display data may include the data trend image data associated with a selected lab panel. In such embodiments, the displayed enhanced image is the data trend image of the selected lab panel.

In other embodiments, the enhanced image display data may include a plurality of data trend image data associated with a respective plurality selected lab panels. In such embodiments, the displayed enhanced image is the data trend images of the selected lab panels.

In accordance with other aspects of the present disclosure, graphs for different test groupings can be displayed side-by-side, and can be moved to overlap one another to compare graphs of different test groupings. This will be described in greater detail with reference to FIGS. 7A-E.

Figure 7A:
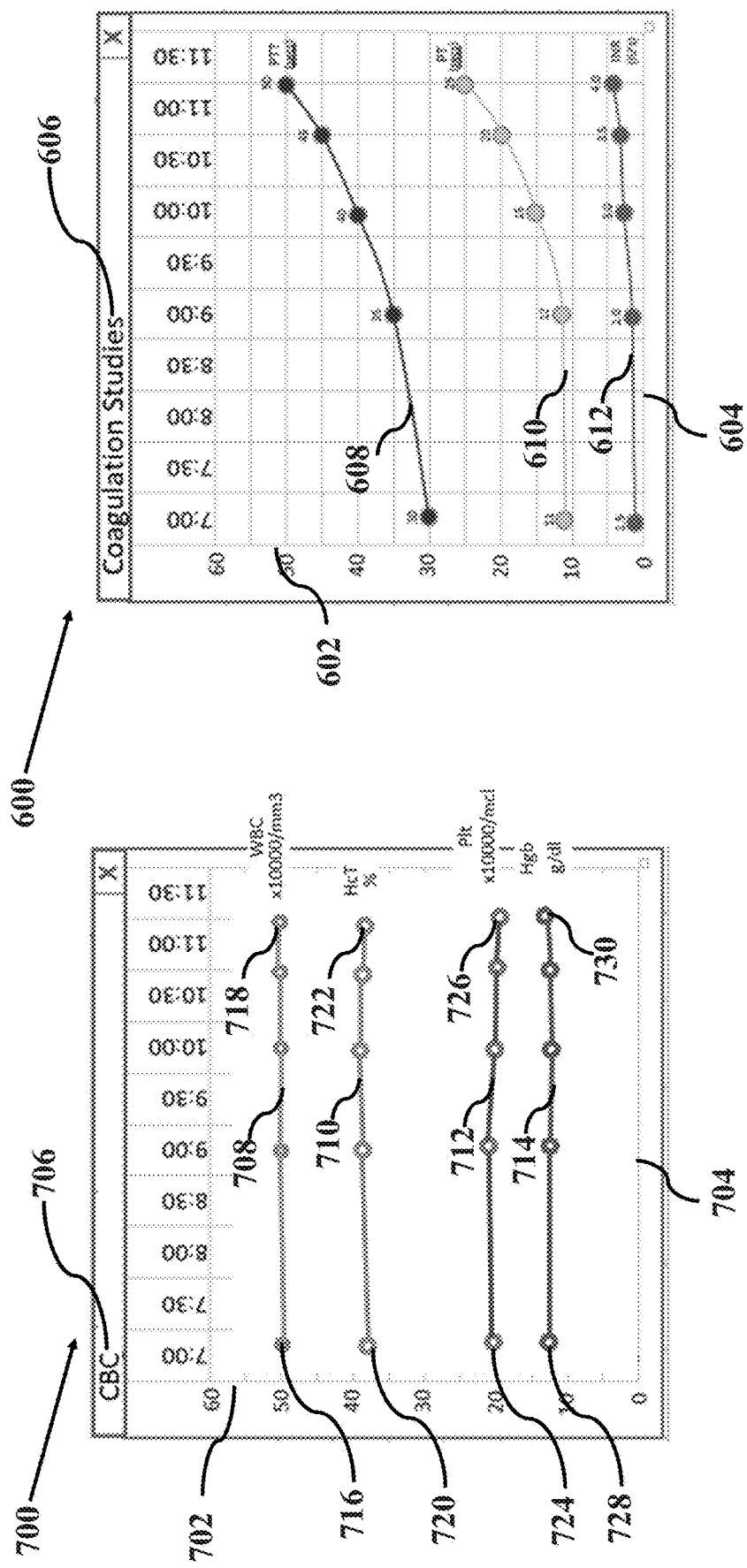
Figure 7B:
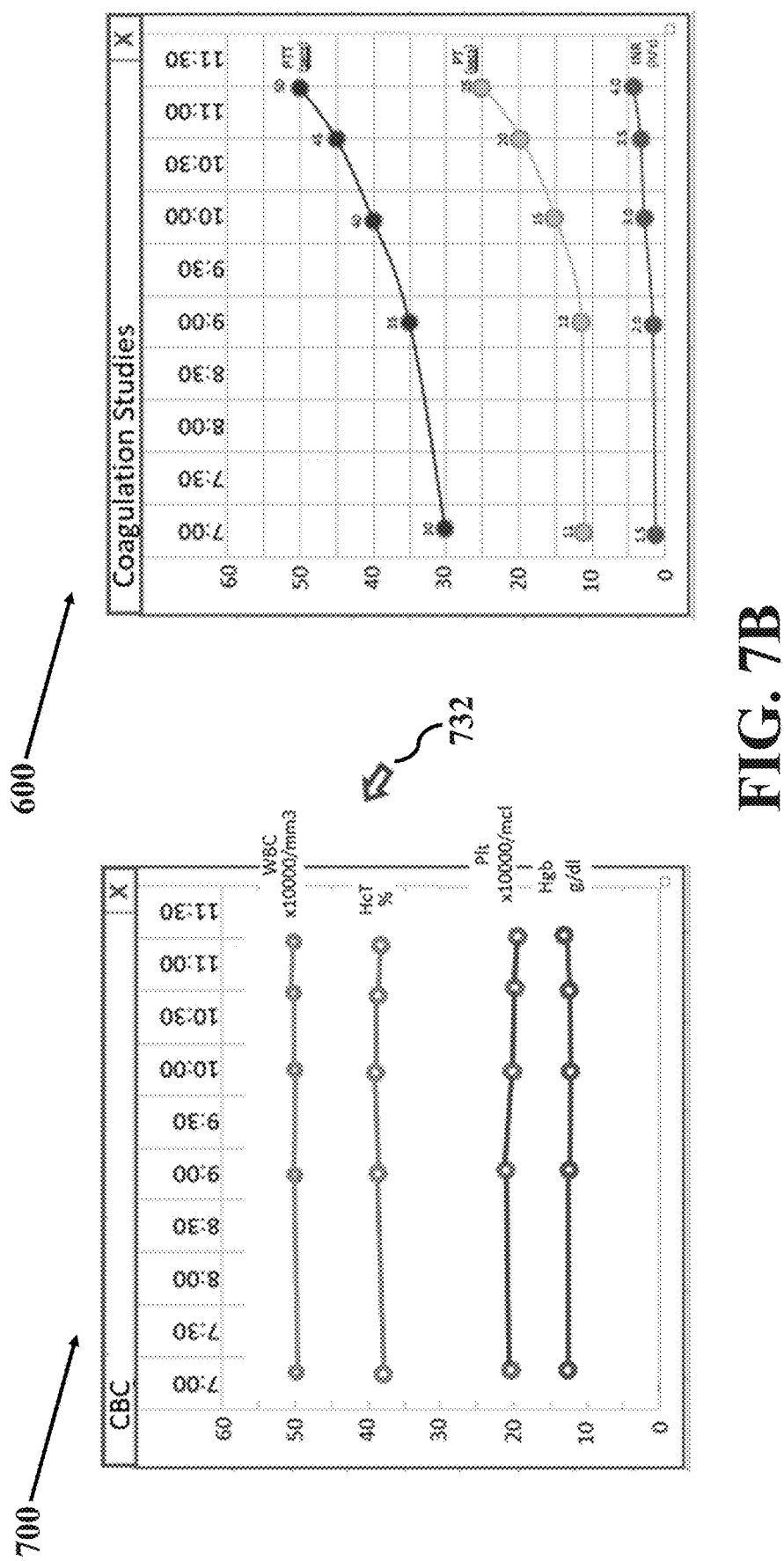
Figure 7C:
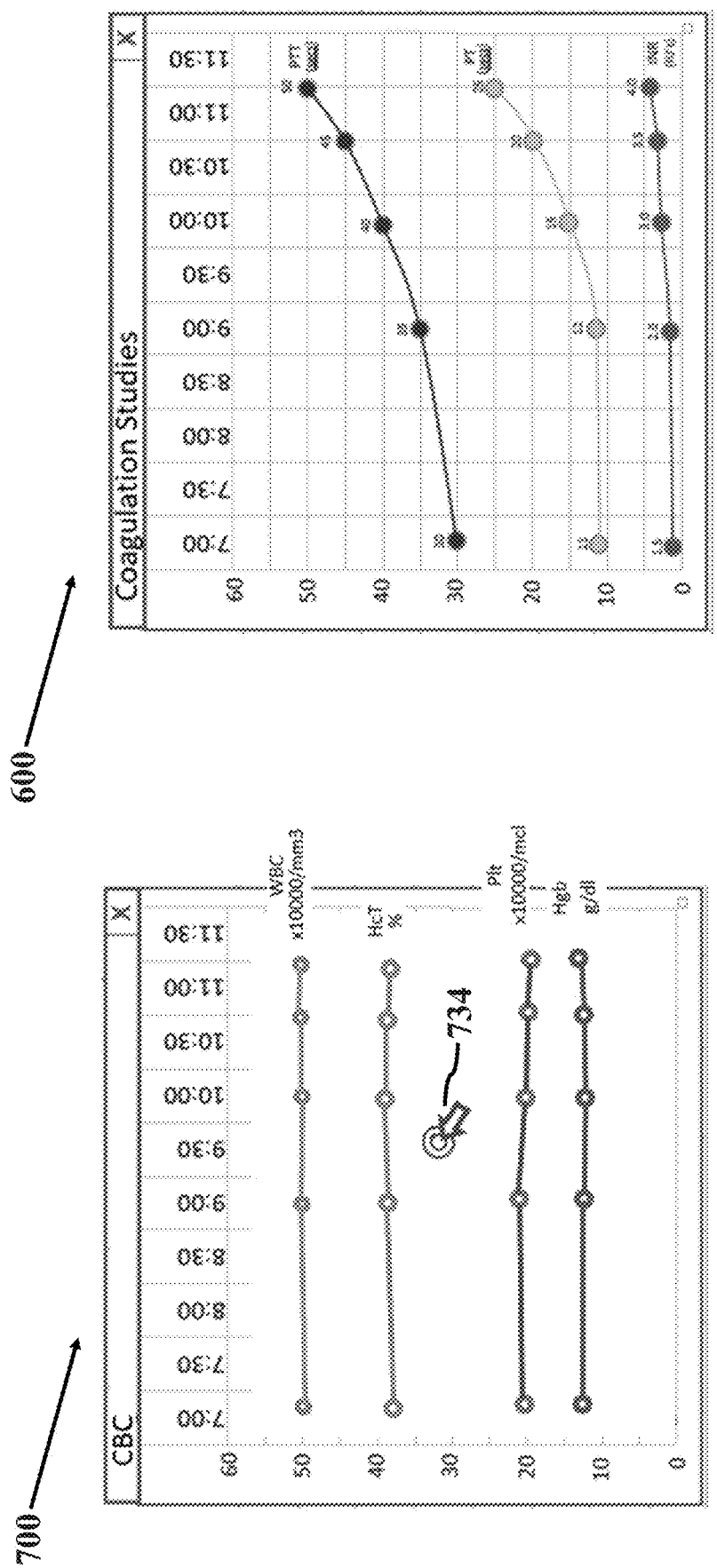
Figure 7D:
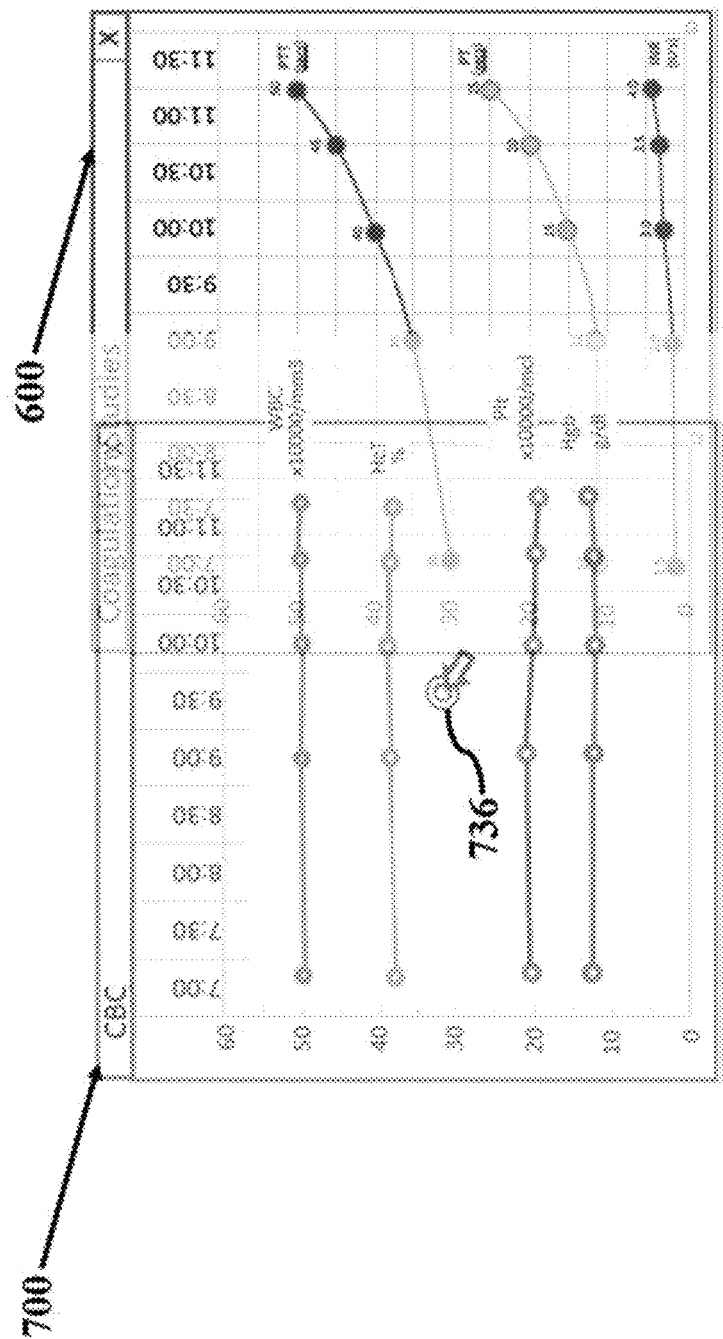
Figure 7E:
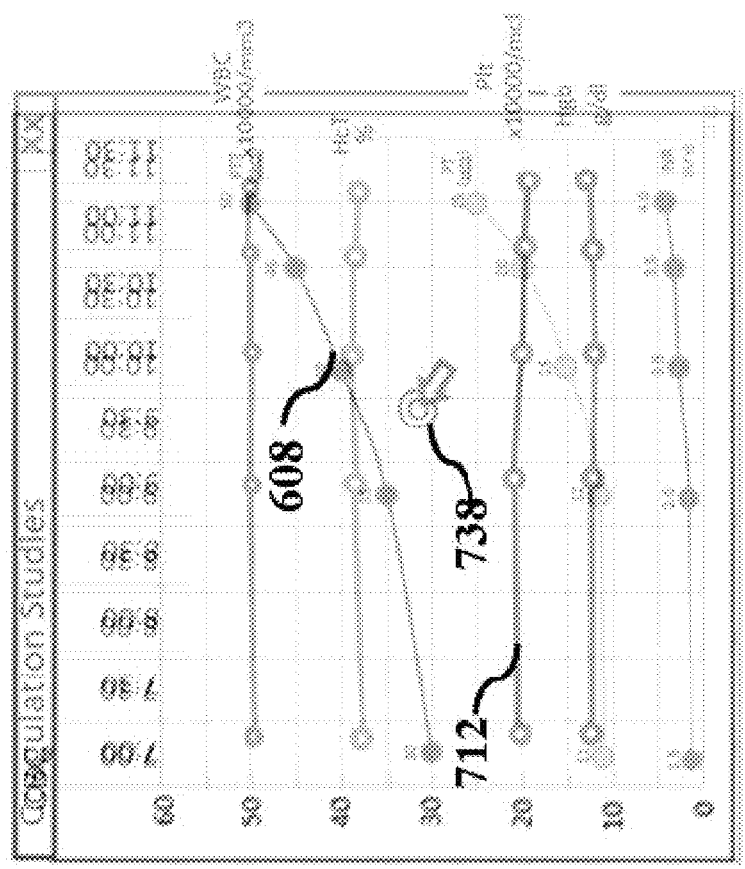

FIGS. 7A-E illustrates an example method of overlaying data trend images in accordance with aspects of the present disclosure. FIG. 7A illustrates example data trend image 600 and an example data trend image 700 at a time $t_a$. FIG. 7B illustrates example data trend image 600 and example data trend image 700 at a time $t_b$. FIG. 7C illustrates example data trend image 600 and example data trend image 700 at a time $t_c$. FIG. 7D illustrates example data trend image 600 and example data trend image 700 at a time $t_d$. FIG. 7E illustrates example data trend image 600 and example data trend image 700 at a time $t_e$.

By displaying overlapping data trend images of multiple parameters, an anesthesia provider is able to easily see a relation of trends of data between multiple different individual sets of patient laboratory test data of multiple parameters, which may not be readily apparent to the anesthesia provider by merely viewing the stand-alone values in a table form, thereby allowing the anesthesia provider to determine if a modified anesthesia service is required.

As shown in FIG. 7A, data trend image 700 includes a y-axis 702, an x-axis 704, a title 706, a function 708, a function 710, a function 712 and a function 714. Function 708 comprises a plurality of data points connected by interpolating connecting lines, wherein the plurality of data points include an initial data point 716 and a most recently received data point 718. Function 710 comprises a plurality of data points connected by interpolating connecting lines, wherein the plurality of data points include an initial data point 720 and a most recently received data point 722. Function 712 comprises a plurality of data points connected by interpolating connecting lines, wherein the plurality of data points include an initial data point 724 and a most recently received data point 726. Function 714 comprises a plurality of data points connected by interpolating connecting lines, wherein the plurality of data points include an initial data point 728 and a most recently received data point 730. It should be understood that the present disclosure is not limited to FIGS. 7A-E and at least one of the values, units and scales of the overlaying data trend images may have different configuration settings as appropriate.

In this example embodiment, function 708 corresponds to a fourth patient laboratory test data corresponding to a fourth measurable parameter of the patient. For purposes of discussion, let function 708 correspond to the measured WBC of the patient. As such, initial data point 716 corresponds to the first measured WBC provided at 7:00, whereas most recently received data point 718 corresponds to the most recently measured WBC provided at 11:15.

In this example embodiment, function 710 corresponds to a firth patient laboratory test data corresponding to a fifth measurable parameter of the patient. For purposes of discussion, let function 710 correspond to the measured HcT of the patient. As such, initial data point 720 corresponds to the first measured HcT provided at 7:00, whereas most recently received data point 722 corresponds to the most recently measured HcT provided at 11:15.

In this example embodiment, function 712 corresponds to a sixth patient laboratory test data corresponding to a sixth measurable parameter of the patient. For purposes of discussion, let function 712 correspond to the measured Plt of the patient. As such, initial data point 724 corresponds to the first measured Plt provided at 7:00, whereas most recently received data point 726 corresponds to the most recently measured Plt provided at 11:15.

In this example embodiment, function 714 corresponds to a seventh patient laboratory test data corresponding to a seventh measurable parameter of the patient. For purposes of discussion, let function 714 correspond to the measured Hgb of the patient. As such, initial data point 728 corresponds to the first measured Hgb provided at 7:00, whereas most recently received data point 730 corresponds to the most recently measured Hgb provided at 11:15.

In this example, the WBC, the HcT, the Plt and Hgb have different units of measure. Accordingly, in order to use a single common y-axis 702 to display functions 708, 710, 712 and 714, the units for each function may be illustrated next to the respective functions. However, the units of each function may be adjusted by appropriate factors of 10 so as to use y-axis 702, which in this example ranges from a value of 0-60.

Just as with data trend image 600 as discussed above, with data trend image 700, an anesthesia provider can see: the most recent received values of patient laboratory test data for a plurality of measurable parameters; all the historical received values of patient laboratory test data for a plurality of measurable parameters; the combination of the most recent received values of patient laboratory test data for a plurality of measurable parameters and all the historical received values of patient laboratory test data for a plurality of measurable parameters; trends in the patient laboratory test data.

Further, just as with data trend image 600 discussed above, data trend image 700 permits an anesthesia provider to see: a trend of data for an individual set of patient laboratory test data of a single parameter; and a relation of trends of data between multiple individual sets of patient laboratory test data of multiple parameters.

In accordance with another aspect of the present disclosure, an anesthesia provider is able to view a combination of plural data trend images so as to see a relation of trends of data between multiple individual sets of different types of patient laboratory test data of multiple parameters. This will be described in greater detail below with reference to FIGS. 7B-E.

FIG. 7B illustrates example data trend image 600 and example data trend image 700 at a time $t_b$. In FIG. 7B, a user is able to select one of data trend image 600 and data trend image 700 using any known input device. In this example, the user is using a mouse (not shown) as UI system 210 that is able to move a selecting arrow 732.

FIG. 7C illustrates example data trend image 600 and example data trend image 700 at a time $t_c$. In FIG. 7C, the user selects data trend image 700, as shown by selecting arrow 734.

FIG. 7D illustrates example data trend image 600 and example data trend image 700 at a time $t_d$. In FIG. 7D, the user has dragged data trend image 700 over a portion of data trend image 600, as shown by selecting arrow 736. In this embodiment, data trend image 700 is at least partially transparent so that the portion of data trend image 600 that is overlapped by a portion of data trend image 700 is still visible.

FIG. 7E illustrates example data trend image 600 and example data trend image 700 at a time $t_e$. In FIG. 7E, the user has dragged data trend image 700 over so as to cover the entirety of data trend image 600, as shown by selecting arrow 738. In this embodiment, data trend image 700 is at least partially transparent so that data trend image 600 is still visible.

Further, having data trend image 700 overlap data trend image 600 permits an anesthesia provider to see a relation of trends of data between multiple different individual sets of patient laboratory test data of multiple parameters. For example, the anesthesia provider may see that the measured PTT of the patient, as shown by function 608, is increasing with time and that the measured Plt of the patient, as shown by function 712, is decreasing somewhat with time. Still further, the anesthesia provider may see that the rate measured PTT of the patient, as shown by function 608, is increasing with time in a manner that is much greater as compared to the amount at which the rate of the measured Plt of the patient, as shown by function 712, is decreasing with time. Such relative rates of different sets of laboratory test data for respective different measured parameters might not be readily apparent to the provider by merely viewing the stand-alone values in a table form, for example as shown in display section 504 of FIG. 5.

It should be understood that the present disclosure is not limited to the exemplary embodiment illustrated in FIGS. 7A-E. For different parameters, at least one of the corresponding graphic representation of data trends with respect to values may be different, such that when the anesthesia provider reviews side-by-side, or overlay multiple fishbone diagrams and/or corresponding trend graphs, the values, units, scales for different parameters are clear to be viewed.

Returning to FIG. 3, after the data trend image data is displayed (S322), method 300 stops (S316).

In summary a system for anesthesia information management in accordance with aspects of the present disclosure enables an anesthesia provider to: 1) see the most recent values of measurable parameters of the patient as provided by lab panels; 2) see all historical values of the measurable parameters of the patient: and 3) to view trend data associated with the measurable parameters of the patient.

A system and method in accordance with aspects of the present disclosure provides an anesthesia provider with the ability to review pertinent and related patient laboratory data at a glance without the need to sort through lists of data that are not provided in a logical clinically relevant way. Fishbone diagrams may be updated with current data as available, historical data may be represented in a clinically relevant tabular format and graphic representation of trends within data sets are provided.

The foregoing description of various preferred embodiments have been presented for purposes of illustration and description. It is not intended to be exhaustive or to limit the disclosure to the precise forms disclosed, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the invention be defined by the claims appended hereto.

The invention claimed is:

1. An anesthesia information management system for displaying a plurality of patient laboratory test data of a patient, the system comprising:
   an anesthesia information management component, including:
     a data input component for receiving the plurality of patient laboratory test data through a communication channel during a procedure including anesthesia care, the plurality of patient laboratory test data including patient care information acquired during the anesthesia care and at least one of:
       a set of first patient laboratory test data received from a first data provider, and
       a set of second patient laboratory test data received from a second data provider;
   a user interface component configured to receive an instruction from a user, and a display device configured to:
     display one or more fishbone diagrams, each of the one or more fishbone diagrams including a plurality of sections for displaying the plurality of patient laboratory test data;
     upon receiving the instruction from the user via the user interface component, display on the display device the patient laboratory test data and time-stamps indicating time of collection in the one or more fishbone diagrams; and
     concurrently display in a single view with the patient laboratory test data and time stamps in the one or more fishbone diagrams at least one of a first set of historical trend data of the first patient laboratory test data and a second set of historical trend data of the second patient laboratory test data, the displayed first set of historical trend data and the second set of historical trend data providing real-time feedback on treatment decisions.

2. The anesthesia information management system of claim 1, wherein the one or more fishbone diagrams include:
   first image data associated with the first patient laboratory test data, the first image data including a most recently received value of a first measurable parameter; and
   second image data associated with the second patient laboratory test data, the second image data including a most recently received value of a second measurable parameter.

3. The anesthesia information management system of claim 2, wherein the one or more fishbone diagrams further include:
   a first time associated with the most recently received value of the first measurable parameter and a first unit of measure of the first measurable parameter; and
   a second time associated with the most recently received value of the second measurable parameter and a second unit of measure of the second measurable parameter.

4. The anesthesia information management system of claim 3, wherein:
the first time associated with the most recently received value of the first measurable parameter includes at least one of:
when the most recently received value of the first measurable parameter was obtained,
when the most recently received value of the first measurable parameter was measured, and
when the most recently received value of the first measurable parameter was provided, and
the second time associated with the most recently received value of the second measurable parameter includes at least one of:
when the most recently received value of the second measurable parameter was obtained,
when the most recently received value of the second measurable parameter was measured, and
when the most recently received value of the second measurable parameter was provided.

5. The anesthesia information management system of claim 1, wherein:
the historical trend data of the first patient laboratory test data is displayed as a first table corresponding to the first patient laboratory test data, and
the historical trend data of the second patient laboratory test data is displayed as a second table corresponding to the second patient laboratory test data.

6. The anesthesia information management system of claim 5, wherein the first table corresponding to the first patient laboratory test data and the second table corresponding to the second patient laboratory test data each include additional table information corresponding to additional patient laboratory test data.

7. The anesthesia information management system of claim 1, wherein the first patient laboratory test data provided from the first data provider and the second patient laboratory test data provided from the second data provider are each provided from a single data provider.

8. The anesthesia information management system of claim 1, wherein:
the historical trend data of the first patient laboratory test data is displayed as a first line graph corresponding to the first patient laboratory test data, and
the second patient laboratory test data is displayed as a second line graph corresponding to the second patient laboratory test data.

9. A method for displaying a plurality of patient laboratory test data of a patient in an anesthesia information management system, the method comprising:
receiving over a communication channel, using a data input component, the plurality of patient laboratory test data during a procedure including anesthesia care, the plurality of patient laboratory test data including operative care information acquired during the anesthesia care and at least one of:
a set of first patient laboratory test data received from a first data provider, and
a set of second patient laboratory test data received from a second data provider;
displaying, using a display interface, one or more fishbone diagrams, each of the one or more fishbone diagrams including a plurality of sections for displaying the plurality of patient laboratory test data; and
upon receiving an instruction from a user via a user interface component, displaying with the patient laboratory test data and time-stamps indicating time of collection in the one or more fishbone diagrams; and
concurrently displaying in a single view with the patient laboratory test data and time stamps in the one or more fishbone diagrams at least one of a set of historical trend data of the first patient laboratory test data and a set of historical trend data of the second patient laboratory test data.

10. The method of claim 9, wherein the one or more fishbone diagrams include:
first image data associated with the first patient laboratory test data, the first image data including a most recently received value of a first measurable parameter; and
second image data associated with the second patient laboratory test data, the second image data including a most recently received value of a second measurable parameter.

11. The method of claim 10, wherein the one or more fishbone diagrams further include:
a first time associated with the most recently received value of the first measurable parameter and a first unit of measure of the first measurable parameter; and
a second time associated with the most recently received value of the second measurable parameter and a second unit of measure of the second measurable parameter.

12. The method of claim 11, wherein:
the first time associated with the most recently received value of the first measurable parameter includes at least one of:
when the most recently received value of the first measurable parameter was obtained,
when the most recently received value of the first measurable parameter was measured, and
when the most recently received value of the first measurable parameter was provided, and
the second time associated with the most recently received value of the second measurable parameter includes at least one of:
when the most recently received value of the second measurable parameter was obtained,
when the most recently received value of the second measurable parameter was measured, and
when the most recently received value of the second measurable parameter was provided.

13. The method of claim 9, wherein:
the historical trend data of the first patient laboratory test data is displayed as a first table corresponding to the first patient laboratory test data, and
the historical trend data of the second patient laboratory test data is displayed as a second table corresponding to the second patient laboratory test data.

14. The method of claim 13, wherein the first table corresponding to the first patient laboratory test data and the second table corresponding to the second patient laboratory test data each include additional table information corresponding to additional patient laboratory test data.

15. The method of claim 9, wherein the first patient laboratory test data provided from the first data provider and the second patient laboratory test data provided from the second data provider are each provided from a single data provider.

16. The method of claim 9, wherein:
the historical trend data of the first patient laboratory test data is displayed as a first line graph corresponding to the first patient laboratory test data, and the second patient laboratory test data is displayed as a second line graph corresponding to the second patient laboratory test data.

17. A non-transitory computer readable recoding medium having stored thereon executable instructions, that when executed by a processor in an anesthesia information management system, cause the anesthesia information management system to display a plurality of patient laboratory test data of a patient to perform a method comprising:
receiving over a communication channel during a procedure including anesthesia care, using a data input component of an anesthesia information management component, the plurality of patient laboratory test data, the plurality of patient laboratory test data including at least one of:
a set of first patient laboratory test data provided by a first data provider, and
a set of second patient laboratory test data received from a second data provider;
displaying, using a display interface, one or more fishbone diagrams, each of the one or more fishbone diagrams including a plurality of sections for displaying the plurality of patient laboratory test data;
upon receiving an instruction from a user via a user interface component, concurrently displaying in full size with the patient laboratory test data and timestamps indicating time of collection in the one or more fishbone diagrams; and
concurrently displaying in a single view with the patient laboratory test data and time stamps in the one or more fishbone diagrams at least one of a set of historical trend data of the first patient laboratory test data and a set of historical trend data of the second patient laboratory test data.

18. The non-transitory computer readable recoding medium of claim 17, wherein the one or more fishbone diagrams include:
first image data associated with the first patient laboratory test data, the first image data including a most recently received value of a first measurable parameter, and
second image data associated with the second patient laboratory test data, the second image data including a most recently received value of a second measurable parameter.

19. The non-transitory computer readable recoding medium of claim 18, wherein the one or more fishbone diagrams further include:
a first time associated with the most recently received value of the first measurable parameter and a first unit of measure of the first measurable parameter, and
a second time associated with the most recently received value of the second measurable parameter and a second unit of measure of the second measurable parameter.

20. The non-transitory computer readable recoding medium of claim 19, wherein:
the first time associated with the most recently received value of the first measurable parameter includes at least one of:
when the most recently received value of the first measurable parameter was obtained,
when the most recently received value of the first measurable parameter was measured, and
when the most recently received value of the first measurable parameter was provided, and
the second time associated with the most recently received value of the second measurable parameter includes at least one of:
when the most recently received value of the second measurable parameter was obtained,
when the most recently received value of the second measurable parameter was measured, and
when the most recently received value of the second measurable parameter was provided.

21. The non-transitory computer readable recoding medium of claim 17, wherein:
the historical trend data of the first patient laboratory test data is displayed as a first table corresponding to the first patient laboratory test data, and the historical trend data of the second patient laboratory test data is displayed as a second table corresponding to the second patient laboratory test data.

22. The non-transitory computer readable recoding medium of claim 21, wherein the first table corresponding to the first patient laboratory test data and the second table corresponding to the second patient laboratory test data each include additional table information corresponding to additional patient laboratory test data.

23. The non-transitory computer readable recoding medium of claim 17, wherein the first patient laboratory test data provided from the first data provider and the second patient laboratory test data provided from the second data provider are each provided from a single data provider.

24. The non-transitory computer readable recoding medium of claim 17, wherein:
the historical trend data of the first patient laboratory test data is displayed as a first line graph corresponding to the first patient laboratory test data, and
the second patient laboratory test data is displayed as a second line graph corresponding to the second patient laboratory test data.

25. The anesthesia information management system of claim 1, wherein the concurrent display in the single view of the first set of historical trend data and the second set of historical trend data includes:
concurrently displaying both of the first set of historical trend data and the second set of historical trend data in a single view with the patient laboratory test data and the time stamps; and
overlaying the display in the first set of historical trend data with the display of the second set of historical trend data.

26. The method of claim 9, wherein concurrent displaying in the single view of the first set of historical trend data and the second set of historical trend data includes:
concurrently displaying both of the first set of historical trend data and the second set of historical trend data in a single view with the patient laboratory test data and the time stamps; and
overlaying the display in the first set of historical trend data with the display of the second set of historical trend data.

27. The non-transitory computer readable recoding medium of claim 17, wherein concurrent displaying in the single view of the first set of historical trend data and the second set of historical trend data includes:
concurrently displaying both of the first set of historical trend data and the second set of historical trend data in a single view with the patient laboratory test data and the time stamps; and
overlaying the display in the first set of historical trend data with the display of the second set of historical trend data.

* * * * *